(12) United States Patent
Lee et al.

(10) Patent No.: US 11,081,649 B2
(45) Date of Patent: Aug. 3, 2021

(54) COMPOUND FOR ORGANIC ELECTRONIC ELEMENT, ORGANIC ELECTRONIC ELEMENT USING SAME, AND ELECTRONIC DEVICE THEREOF

(71) Applicant: DUK SAN NEOLUX CO., LTD., Cheonan-si (KR)

(72) Inventors: Yun Suk Lee, Seongnam-si (KR); Sun-Hee Lee, Hwaseong-si (KR); Kiho So, Cheonan-si (KR); Hyoung Keun Park, Chuncheon-si (KR); Jonggwang Park, Ulsan (KR); Yeonseok Jeong, Gangwon-do (KR); Junghwan Park, Hwaseong-si (KR); Sunpil Hwang, Ansan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 16/078,733

(22) PCT Filed: Feb. 13, 2017

(86) PCT No.: PCT/KR2017/001529
§ 371 (c)(1),
(2) Date: Aug. 22, 2018

(87) PCT Pub. No.: WO2017/146405
PCT Pub. Date: Aug. 31, 2017

(65) Prior Publication Data
US 2019/0051840 A1   Feb. 14, 2019

(30) Foreign Application Priority Data
Feb. 23, 2016   (KR) .......................... 10-2016-0020910

(51) Int. Cl.
*H01L 51/00* (2006.01)
*C09K 11/06* (2006.01)
(Continued)

(52) U.S. Cl.
CPC ........ *H01L 51/0068* (2013.01); *C07D 209/88* (2013.01); *C07D 405/04* (2013.01);
(Continued)

(58) Field of Classification Search
CPC ............. H01L 51/0072; H01L 51/5056; H01L 51/5012; H01L 51/5072; C09K 11/06; C07D 209/88; C07D 405/04
(Continued)

(56) References Cited

U.S. PATENT DOCUMENTS

2008/0124572 A1* 5/2008 Mizuki ................. C07C 211/54
428/690

FOREIGN PATENT DOCUMENTS

KR   10-2011-0117548 A   10/2011
KR   10-2011-0129766 A   12/2011
(Continued)

*Primary Examiner* — Tri V Nguyen
(74) *Attorney, Agent, or Firm* — Vorys, Sater, Seymour & Pease LLP; Mih Suhn Koh

(57) ABSTRACT

Provided are a compound represented by Formula 1, an organic electric element comprising a first electrode, a second electrode, and an organic material layer formed between the first electrode and the second electrode and comprising the compound of Formula 1, and an electronic device comprising the element, where the driving voltage of the organic electronic device is lowered, and the luminous efficiency and life time of the organic electronic device is improved.

10 Claims, 1 Drawing Sheet

(51) Int. Cl.

| | |
|---|---|
| *C07D 209/88* | (2006.01) |
| *H01L 51/50* | (2006.01) |
| *C07D 405/04* | (2006.01) |
| *C07D 405/14* | (2006.01) |
| *C07D 409/04* | (2006.01) |
| *C07D 409/14* | (2006.01) |
| *C07D 417/14* | (2006.01) |

(52) U.S. Cl.
CPC ......... *C07D 405/14* (2013.01); *C07D 409/04* (2013.01); *C07D 409/14* (2013.01); *C07D 417/14* (2013.01); *C09K 11/06* (2013.01); *H01L 51/0058* (2013.01); *H01L 51/0059* (2013.01); *H01L 51/0061* (2013.01); *H01L 51/0065* (2013.01); *H01L 51/0067* (2013.01); *H01L 51/0069* (2013.01); *H01L 51/0071* (2013.01); *H01L 51/0072* (2013.01); *H01L 51/0073* (2013.01); *H01L 51/0074* (2013.01); *C09K 2211/1011* (2013.01); *C09K 2211/1014* (2013.01); *C09K 2211/1029* (2013.01); *C09K 2211/1037* (2013.01); *C09K 2211/1088* (2013.01); *C09K 2211/1092* (2013.01); *H01L 51/5012* (2013.01); *H01L 51/5056* (2013.01); *H01L 51/5064* (2013.01); *H01L 51/5072* (2013.01); *H01L 51/5088* (2013.01); *H01L 51/5092* (2013.01); *H01L 51/5096* (2013.01)

(58) Field of Classification Search
USPC .................................................. 252/510, 511
See application file for complete search history.

(56) References Cited

FOREIGN PATENT DOCUMENTS

| | | | | |
|---|---|---|---|---|
| KR | 10-2012-0011445 | A | 2/2012 | |
| KR | 20130102673 | A * | 9/2013 | ............. C09K 11/06 |
| KR | 10-2014-0073412 | A | 6/2014 | |
| KR | 10-1535606 | B1 | 7/2015 | |
| KR | 10-2015-0101942 | A | 9/2015 | |
| KR | 10-2015-0102734 | A | 9/2015 | |
| WO | WO-2014042420 | A1 * | 3/2014 | ............ C07D 409/10 |

* cited by examiner

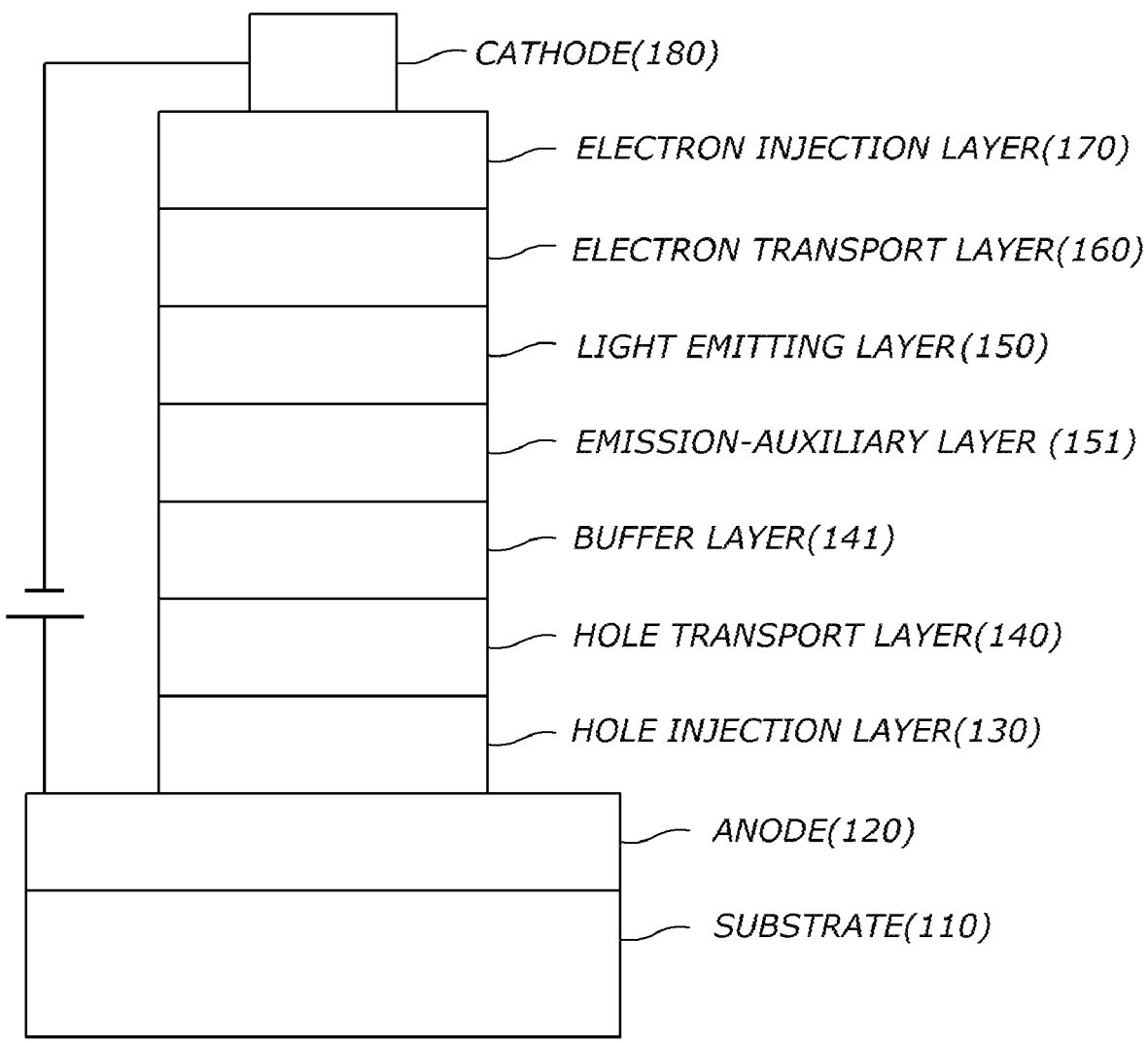

COMPOUND FOR ORGANIC ELECTRONIC ELEMENT, ORGANIC ELECTRONIC ELEMENT USING SAME, AND ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2016-0020910, filed on Feb. 23, 2016, which is hereby incorporated by reference for all purposes as if fully set forth herein. Further, this application claims the benefit of priority in countries other than U.S., which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when energy levels and T1 values among the respective layers included in the organic material layer, inherent material properties (mobility, interfacial properties, etc.) and the like are optimal combination.

Further, an emission-auxiliary layer must be present between the hole transport layer and the light emitting layer in order to solve the problem of luminescence in the hole transport layer of recent organic electroluminescent devices, and it is time to develop different emission-auxiliary layers according to respective light emitting layers (R, G, B).

In general, an electron is transferred from an electron transport layer to a light emitting layer and a hole is transferred from a hole transport layer to the light emitting layer, as a result, an exciton is formed by the recombination of the electron and hole.

However, the material used for the hole transport layer has a low HOMO value and therefore has a low T1 value. As a result, the exciton generated in the light emitting layer is transferred to the hole transport layer, resulting in a charge unbalance in the light emitting layer and light is emitted at the interface of the hole transport layer. Therefore, color purity, the efficiency and lifetime are lowered.

In addition, when a material having a high hole mobility is used to achieving a low driving voltage, the efficiency tends to decrease. Since the hole mobility is faster than the electron mobility in a general organic electroluminescent device, charge unbalance occurs in the light emitting layer, resulting in reduction in efficiency and lifetime.

Therefore, the material of an emission-auxiliary layer has to have a hole mobility for having a proper driving voltage (within a blue device driving voltage range of a full device), a high $T_1$ value and a wide band gap in order to solve the problems of the hole transporting layer. However, this cannot be achieved simply by the structural properties of the core of an emission-auxiliary layer material, but that problem can be solved when the properties of the core and sub-substituents of the material are appropriately combined. Therefore, it is strongly desired to develop a light-emitting auxiliary layer material having a high $T_1$ value and a wide band gap in order to improve efficiency and lifespan of an organic electric element device.

That is, it should be preceded that the materials consisting an organic material layer of the element, for example, a hole injection material, a hole transport material, a light emitting material, an electron transport material, an electron injection material, an emission-auxiliary layer material or the like, are supported by a stable and efficient material. However, such a stable and efficient organic material layer material for an organic electric element has not yet been fully developed. Accordingly, there is a continuous need to develop new materials for an organic material layer, particularly, it is strongly required to develop materials of the emission-auxiliary layer and the hole transport layer.

PRIOR ART

1. Korean Published Patent Application 10-2014-0073412 (16 Jun. 2014)
2. Korean Published Patent Application 10-2015-0101942 (4 Sep. 2015)

Object, Technical Solution and Effects of the Invention

The object of the present invention is to provide a compound capable of lowering the driving voltage of the device and improving the luminous efficiency, heat resistance, color purity and lifespan of a device by improving charge balance due to characteristics such as high $T_1$, deep HOMO energy and high refractive index, wherein the compound of the present invention comprising a carbazole core which is used as a hole transporting material of an organic light emitting diode, and an amine group is substituted at the 2-position of the carbazole and a specific substituent such as dibenzothiophene or dibenzofuran is introduced at the 6-position of the carbazole, an organic electric element comprising the same, and an electronic device thereof.

In accordance with an aspect of the present invention, the compound represented by the following formula is provided.

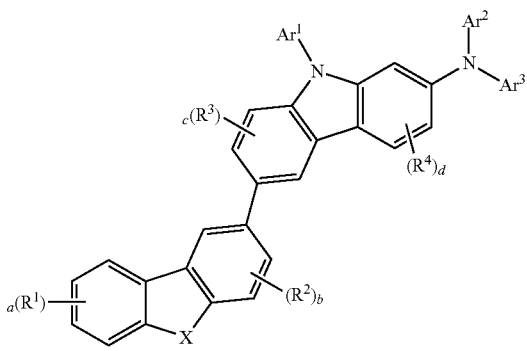

In another aspect of the present invention, organic electric element comprising the compound represented by the above formula and electronic device including the organic electric element are provided.

By using the compound according to embodiments of the present invention, the driving voltage of the element can be lowered, and the luminous efficiency, color purity and lifetime can be remarkably improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine(F), bromine(Br), chlorine(Cl), or iodine(I).

Unless otherwise stated, the term "alkyl" or "alkyl group" as used herein has a single bond of 1 to 60 carbon atoms, and means the saturated aliphatic functional radicals including a linear alkyl group, a branched chain alkyl group, a cycloalkyl group (alicyclic), or an alkyl group substituted with a cycloalkyl or with a cycloalkyl substituted with an alkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

Unless otherwise stated, the term "alkoxyl group", "alkoxy group" or "alkyloxy group" as used herein means an oxygen radical attached to an alkyl group, but not limited to, and has 1 to 60 carbon atoms.

Unless otherwise stated, the term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and it comprises the case where R and R' are bonded to each other to form the spiro compound together with the carbon bonded to them.

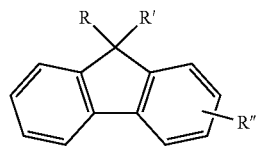

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

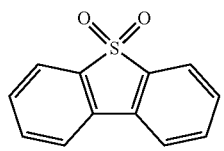

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic ring" as used herein means, ring assemblies such as biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or a combination thereof.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

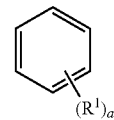

Wherein, when a is an integer of zero, the substituent $R^1$ is absent, that is, hydrogen atoms are bonded to all the carbon constituting the benzene ring, and chemical formulas or compounds may be written without explicitly describing the hydrogen. In addition, one substituent $R^1$ is bonded to any carbon of the carbons forming the benzene ring when "a" is an integer of 1. When "a" is an integer of 2 or 3, for example, substituents $R^1$s are bonded to the carbon of the benzene ring as followings. Also, substituents $R^1$s are bonded to the carbon of the benzene ring when "a" is an integer of 4 to 6 in a similar manner. Further, when "a" is an integer of 2 or more, $R^1$s may be the same or different from each other.

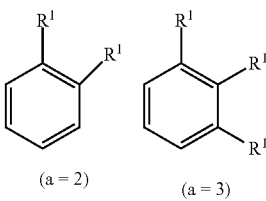

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120.

Here, at least one layer of the organic material layer may be omitted, or the organic material layer may further include a hole blocking layer, an electron blocking layer, an emission-auxiliary layer 151, a buffer layer 141, etc., and the electron transport layer 160 or the like may serve as the hole blocking layer.

Although not shown, the organic electric element according to an embodiment of the present invention may further include a protective layer or a layer for improving luminous efficiency formed on at least one side of sides of the first electrode and the second electrode, wherein at least one side is not facing the organic material layer.

The inventive compound employed in the organic material layer may be used as a material of a hole injection layer 130, a hole transport layer 140, an electron transport auxiliary layer, an electron transport layer 160, an electron injection layer 170, a light emitting layer 150, a layer for improving luminous efficiency, an emission-auxiliary layer 151 and the like. For example, the inventive compound may be used as material of the hole transport layer 140 and/or the emission-auxiliary layer 151.

On the other hand, even if the core is the same core, the band gap, the electrical characteristics, the interface characteristics and the like may be different depending on which substituent is bonded at which position. Therefore, it is necessary to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B). On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

Therefore, according to the present invention, energy level and $T_1$ value between the respective layers of the organic material layer, inherent material properties (mobility, interfacial properties, etc.) and the like can be optimized by forming a hole transport layer and/or an emission-auxiliary layer which comprise the compound represented by the Formula 1, and thus it is possible to simultaneously improve the life span and efficiency of the organic electric element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R(Red), G(Green), B(Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to an aspect of the present invention will be described.

The compound according to an aspect of the present invention is represented by formula 1 below.

[Formula 1]

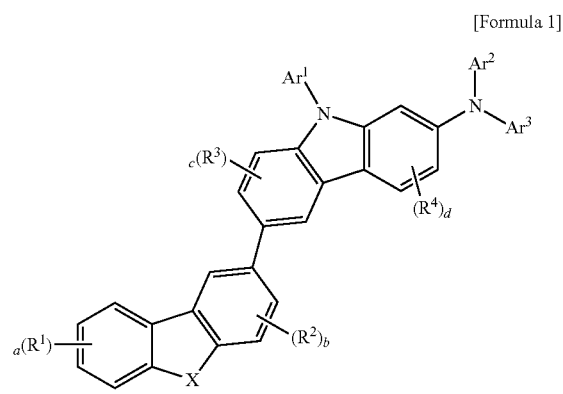

In the formula 1, each of symbols may be defined as follows.

X is O or S.

$R^1$ to $R^4$ may be each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

Further, adjacent $R^1$ groups, adjacent $R^2$ groups, adjacent $R^3$ groups and/or adjacent $R^4$ groups may be optionally bonded to each other to form a ring. Preferably, adjacent groups may be bonded to each other to form a $C_6$-$C_{60}$ aromatic hydrocarbon group, a fluorene, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring and the like.

Preferably, neighboring $R^1$ groups, neighboring $R^2$ groups, neighboring $R^3$ groups and/or neighboring $R^4$ groups can be bonded to each other to form a benzene ring. As a result, benzonaphthofuran or benzophenanthrofuran may be formed with the dibenzofuran to which they are attached, or benzonaphthothiophene or benzophenanthrothiophene may be formed with the dibenzothiophene to which they are attached.

Preferably, the ring formed by bonding between neighboring groups are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

a is an integer of 0 to 4, and b, c and d are each independently an integer of 0 to 3, and a plurality of $R^1$s to a plurality of $R^4$s may be each the same or different from each other when a, b, c and d are each an integer of 2 or more.

$Ar^1$ to $Ar^3$ may be each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$).

When $Ar^1$ to $Ar^3$ are each an aryl group, they may be preferably a $C_6$-$C_{30}$ aryl group, more preferably a $C_6$-$C_{18}$ aryl group, for example, phenyl, biphenyl, terphenyl, naphthalene, phenanthrene or the like; when $Ar^1$ to $Ar^3$ are each a heterocyclic group, they may be preferably a $C_2$-$C_{30}$ heterocyclic group, more preferably a $C_2$-$C_{12}$ heterocyclic group, for example, pyridine, dibenzothiophene, dibenzofuran, carbazole, phenothiazine, or the like; when $Ar^1$ to $Ar^3$ are each a fluorenyl group, they may be preferably 9,9-dimethyl-9H-fluorene, 9,9-diphenyl-9H-fluorene, 9,9'-spirofluorene or the like.

The above L' may be selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

The above $R_a$ and $R_b$ may be each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

The above aryl group, fluorenyl group, heterocyclic group, fused ring group, alkyl group, alkenyl group, alkynyl group, alkoxyl group, aryloxyl group, arylene group and fluorenylene group are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

Specifically, the formula 1 may be represented by the following formulas 2 or 3. The following Formula 2 represents a case where X is S in Formula 1 and the following Formula 3 represents a case where X is O in Formula 1.

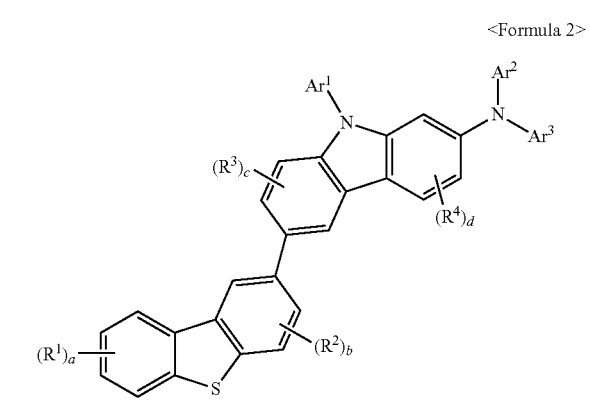

<Formula 2>

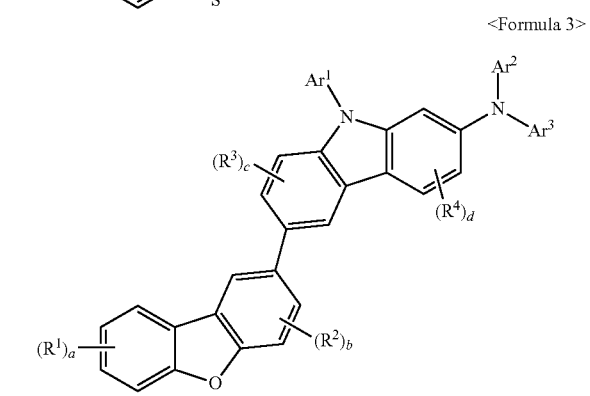

<Formula 3>

In formulas 2 and 3, a, b, c, d, $R^1$ to $R^4$, $Ar^1$ to $Ar^3$ are the same as defined in the Formula 1. Specifically, the formula 1 may be represented by the following formulas 4 to 9. The following Formulas 4 to 9 represent the cases where adjacent $R^1$ groups, adjacent $R^2$ groups, adjacent $R^3$ groups and/or adjacent $R^4$ groups are bonded to each other to form at least one ring.

<Formula 4>
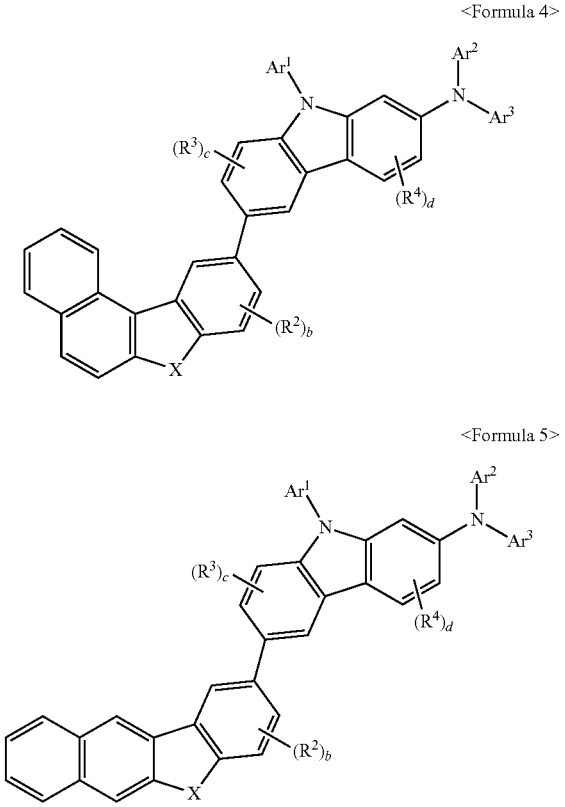
<Formula 5>
<Formula 6>
<Formula 7>
<Formula 8>
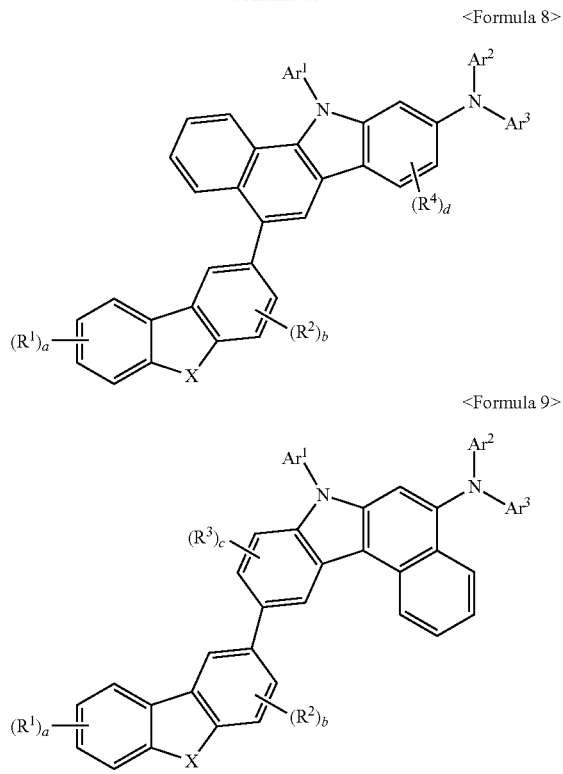
<Formula 9>
In formulas 4 to 9, X, a, b, c, d, $R^1$ to $R^4$, $Ar^1$ to $Ar^3$ are the same as defined in the Formula 1.
More specifically, the compound represented by formula 1 may be any one of the following compounds.
1-1
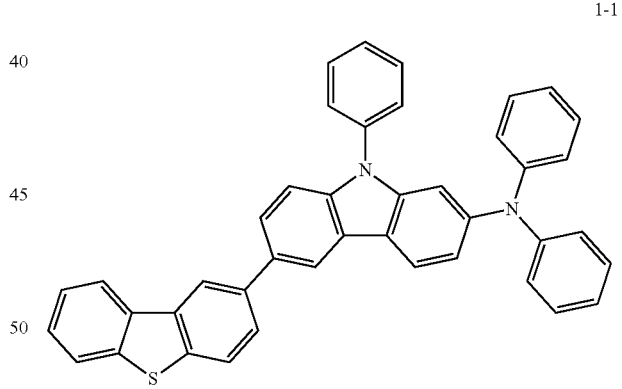
1-2
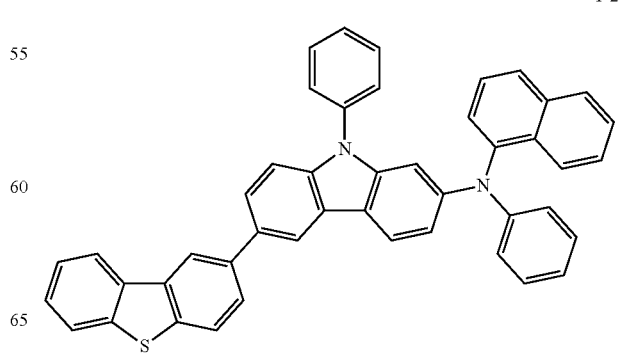

1-3
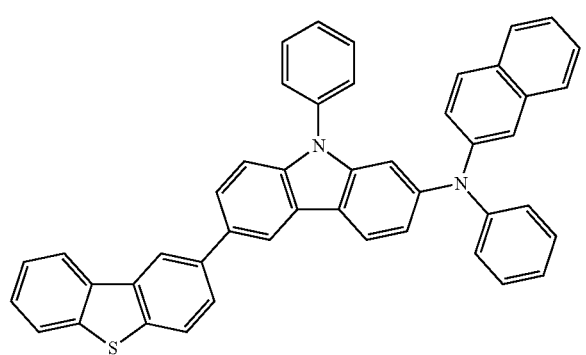
1-7
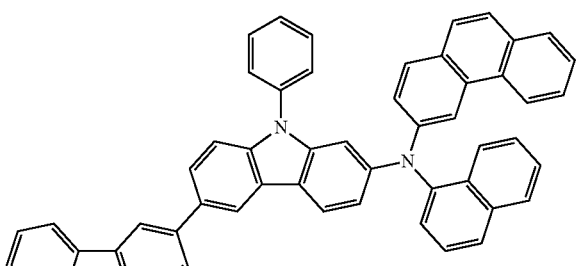
1-4
1-8
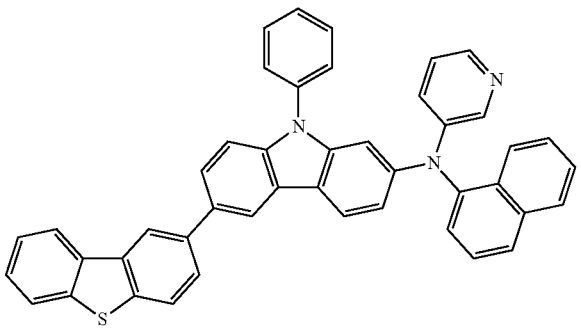
1-5
1-9
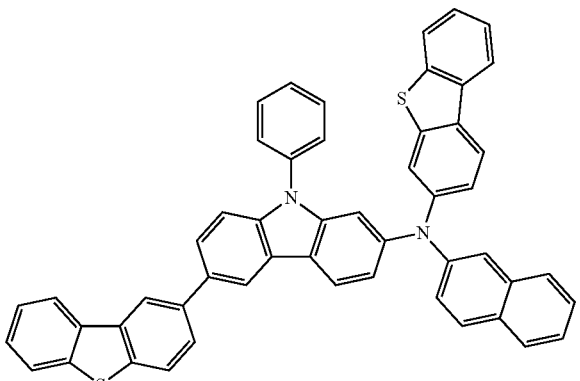
1-6
1-10
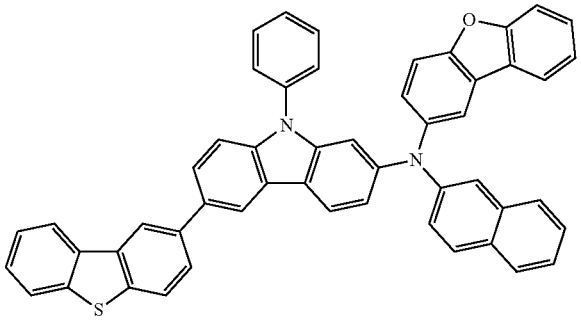

1-11
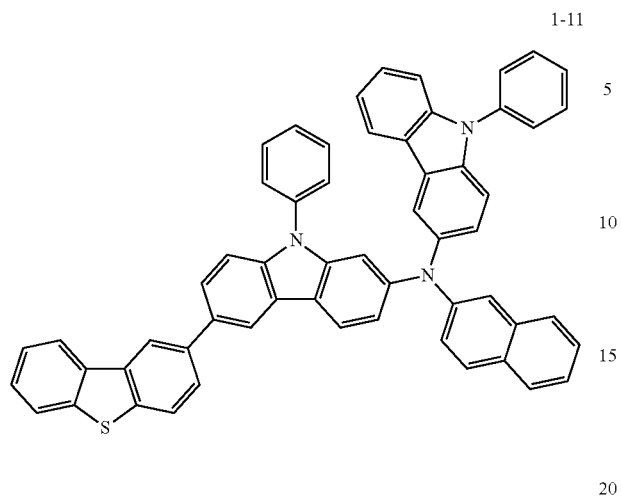
1-14
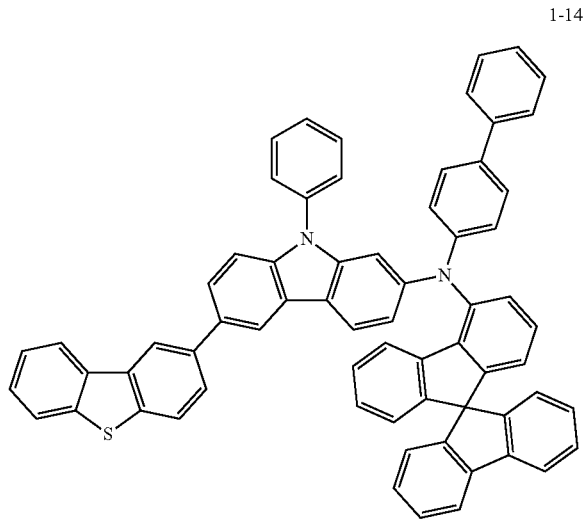
1-12
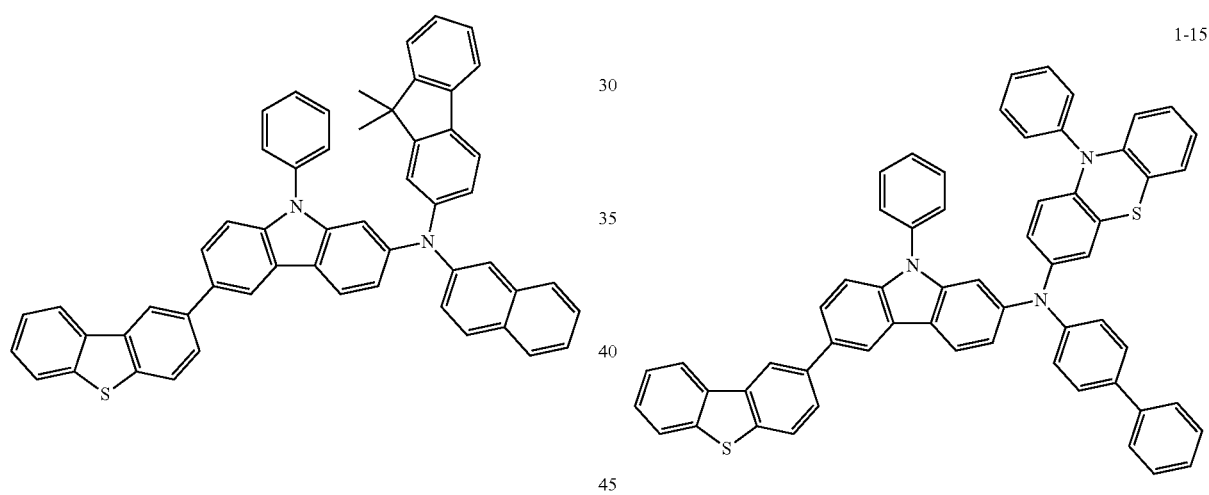
1-15
1-13
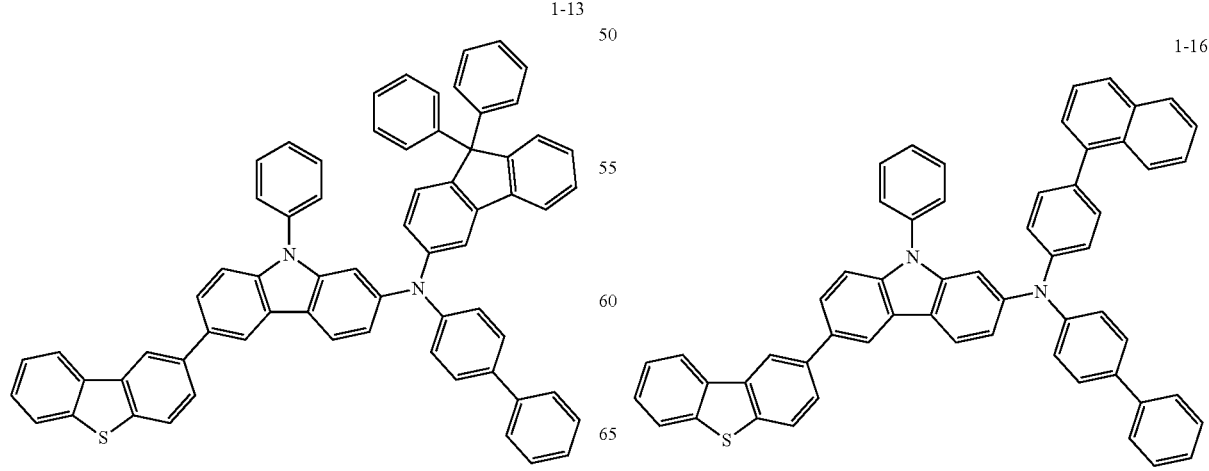
1-16

-continued
1-17
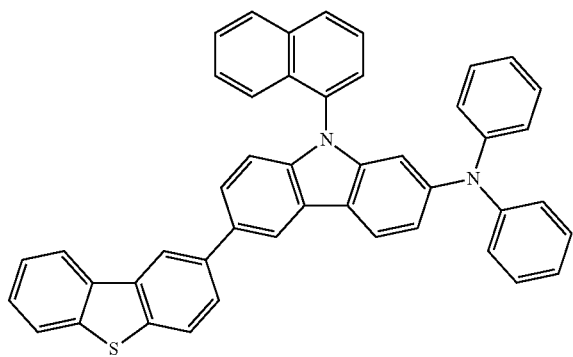
1-18
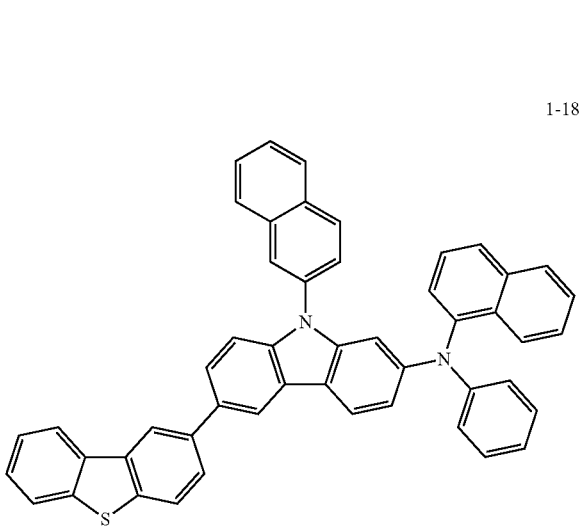
1-19
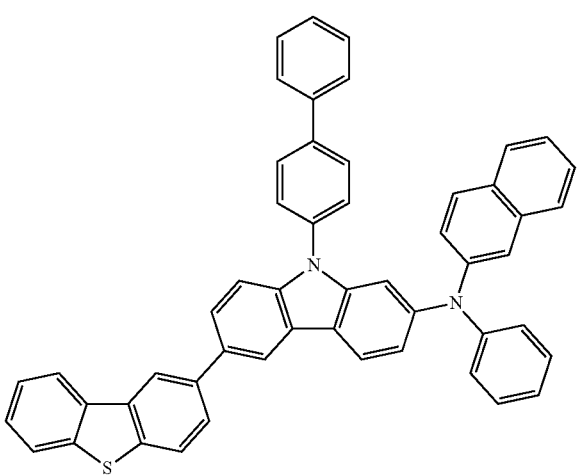
-continued
1-20
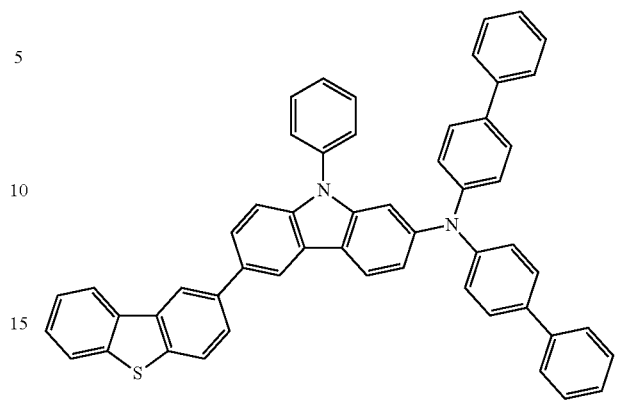
1-21
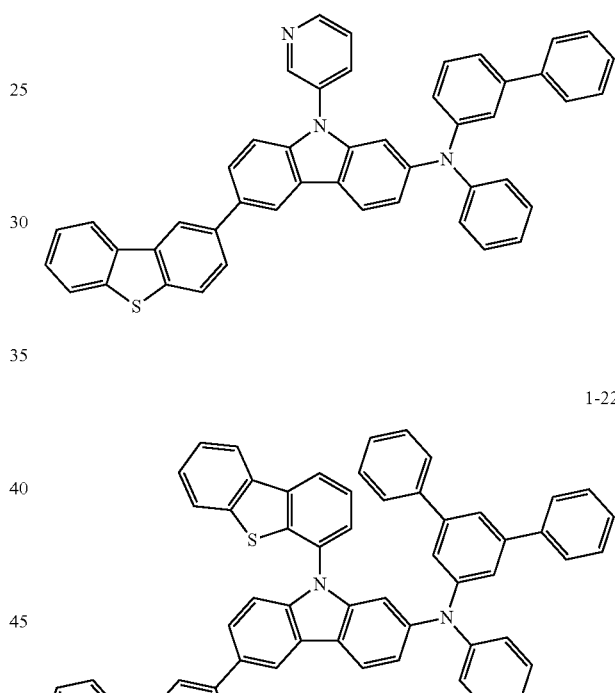
1-22
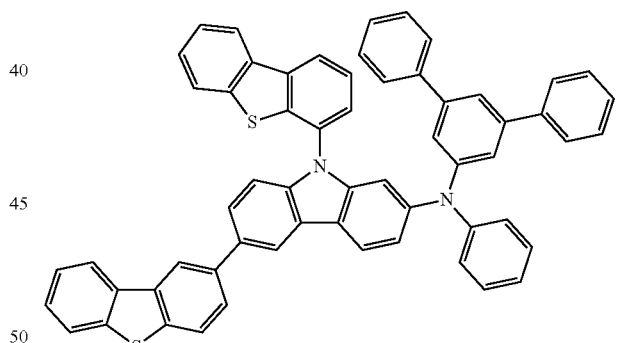
1-23
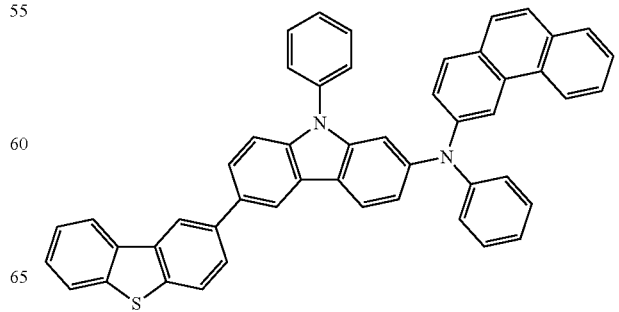

19
-continued
1-24
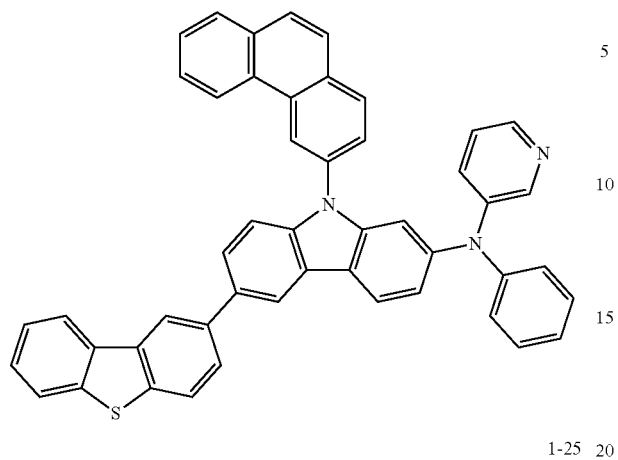
1-25
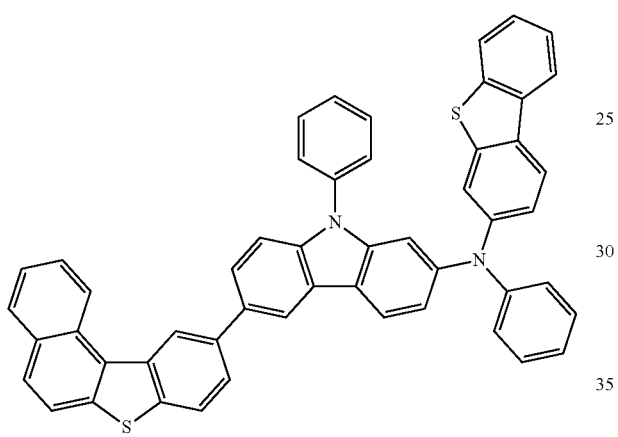
1-26
1-27
20
-continued
1-28
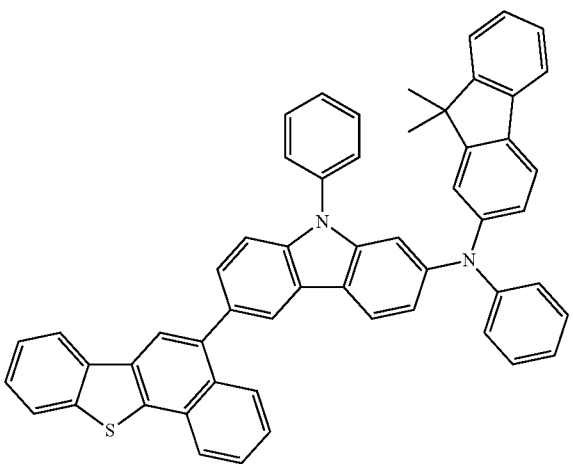
1-29
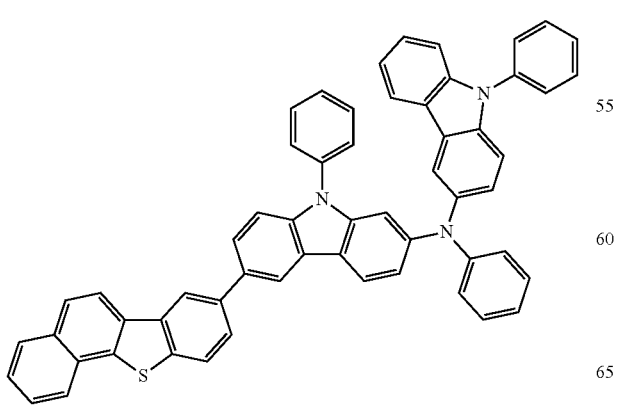
1-30

-continued
1-31
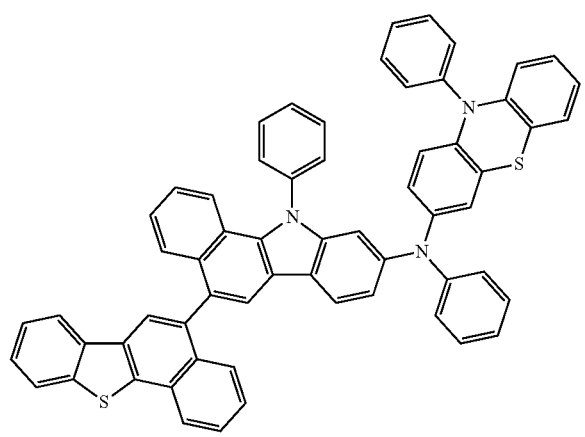
1-32
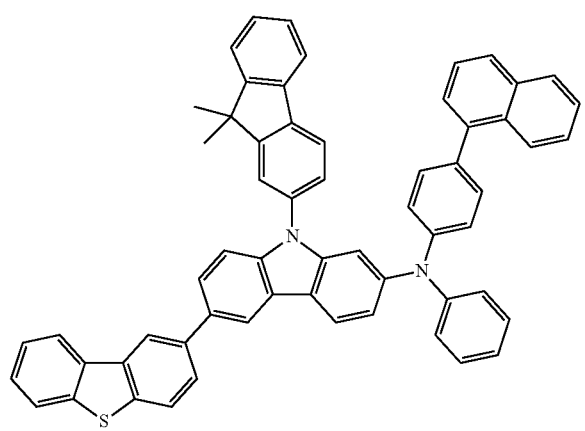
2-1
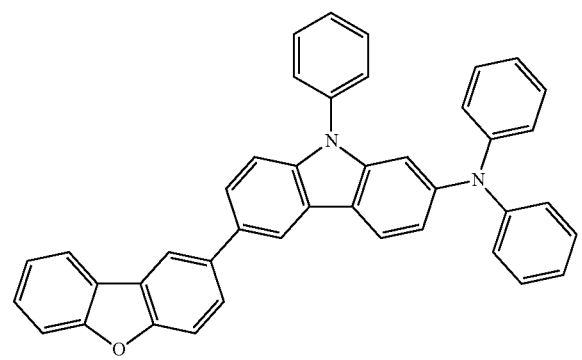
2-2
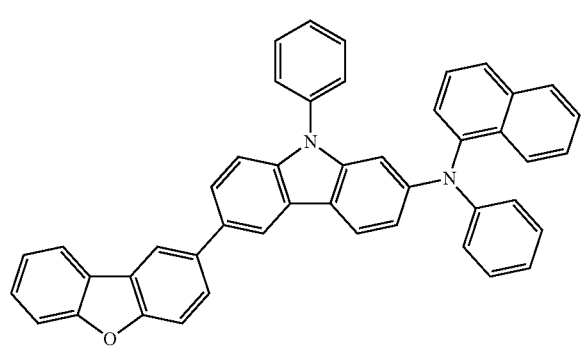
-continued
2-3
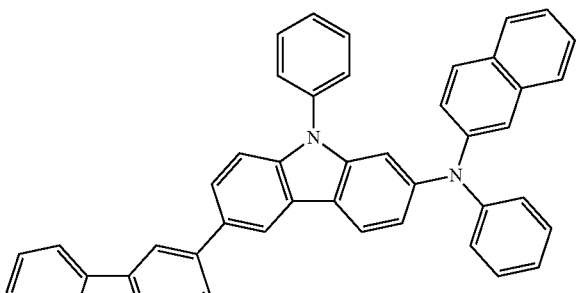
2-4
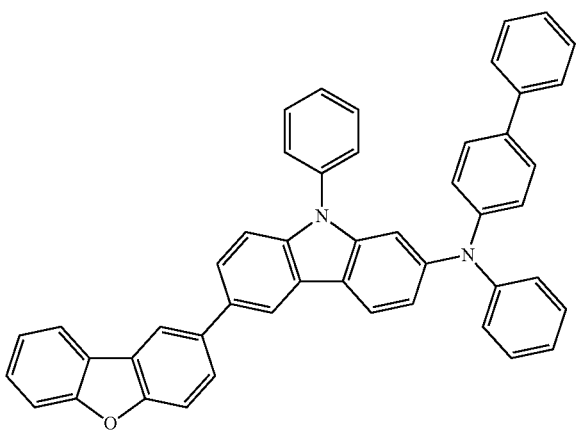
2-5
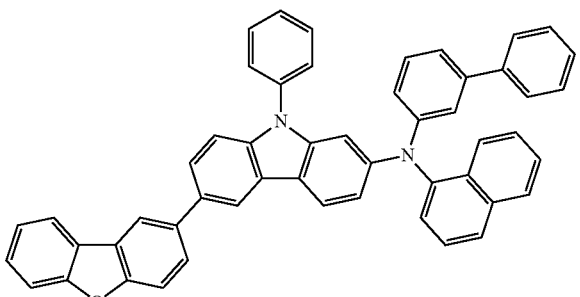
2-6
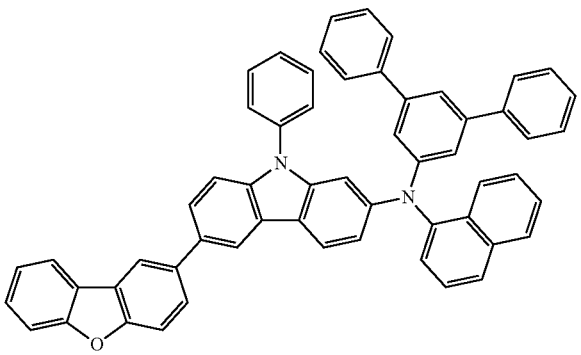

-continued
2-7
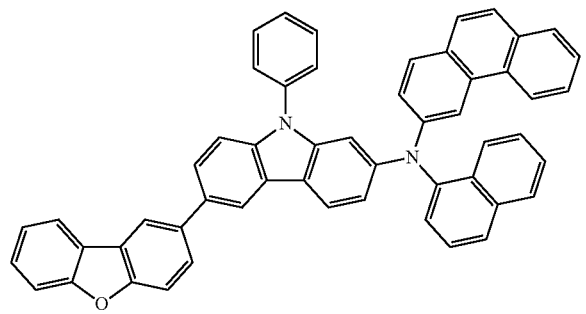
2-8
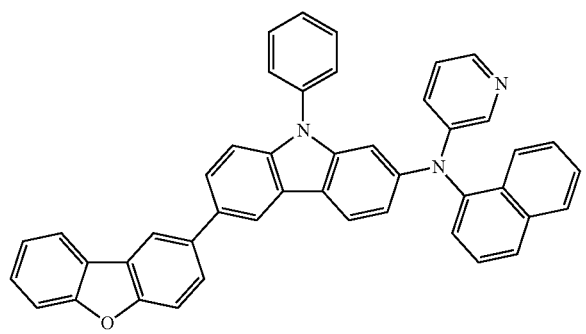
2-9
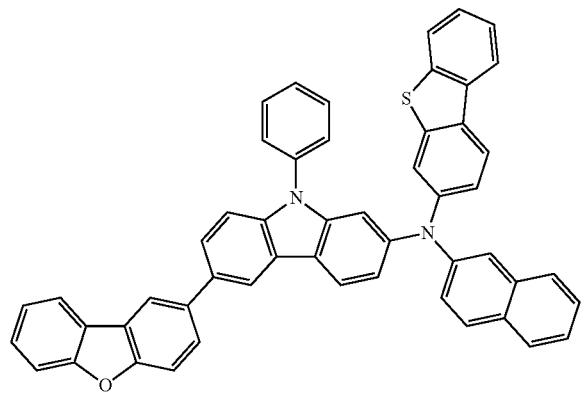
2-10
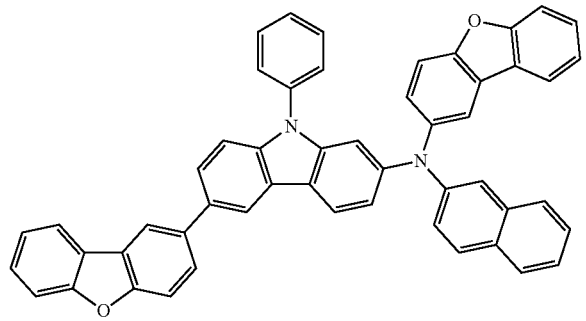
-continued
2-11
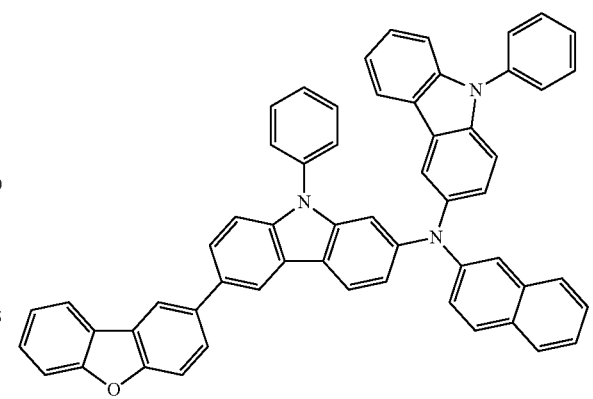
2-12
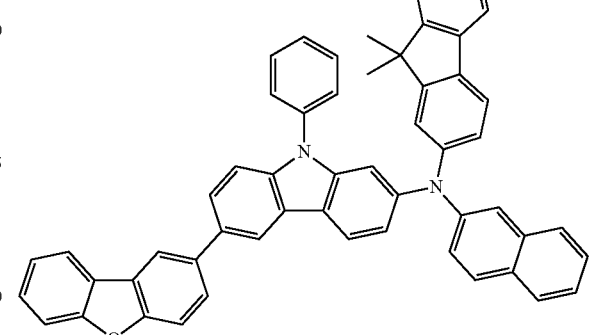
2-13
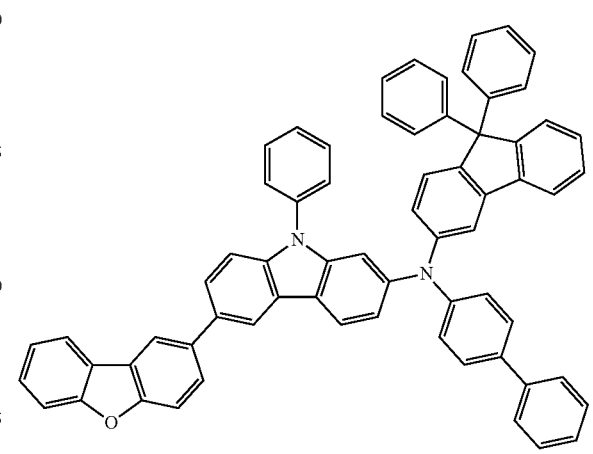

-continued
2-14
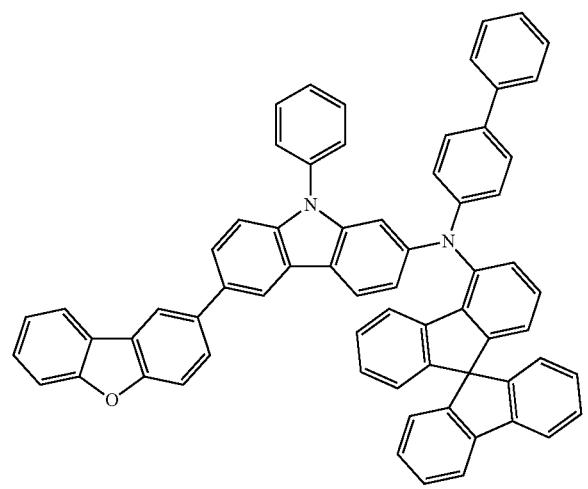
2-17
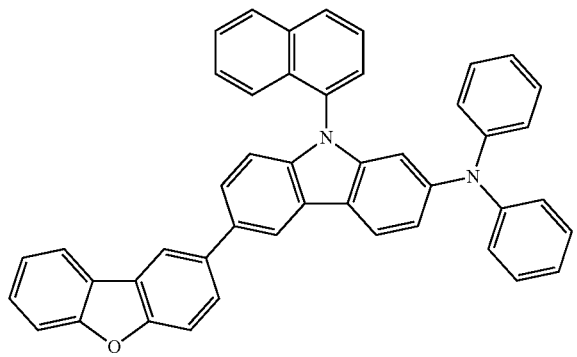
2-15
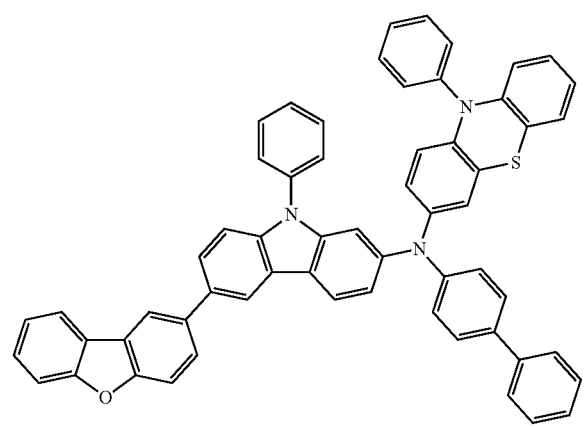
2-18
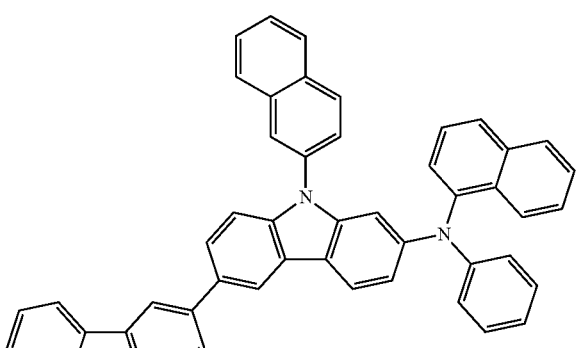
2-16
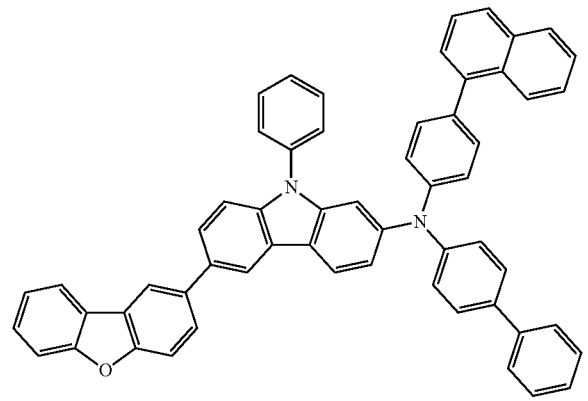
2-19
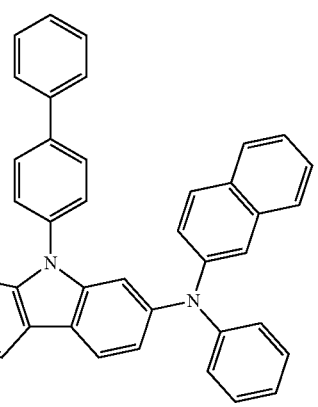

-continued
2-20
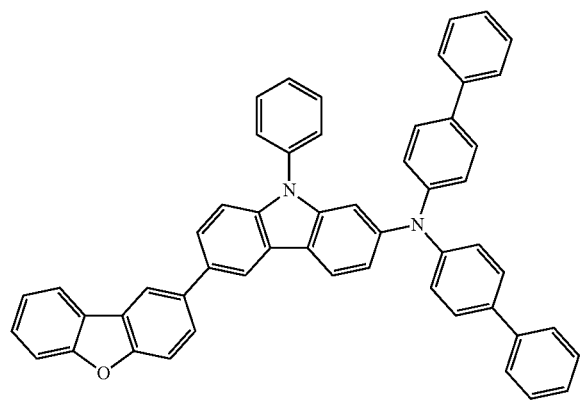
2-21
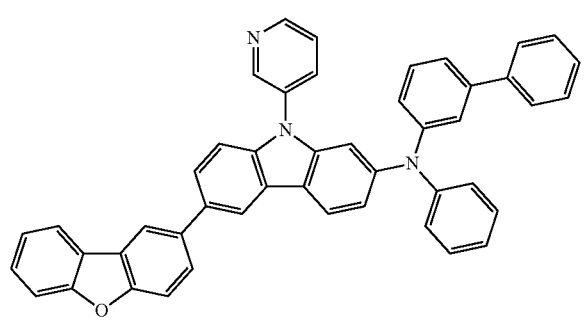
2-22
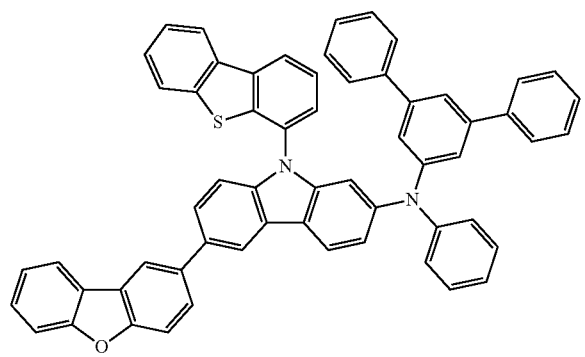
2-23
-continued
2-24
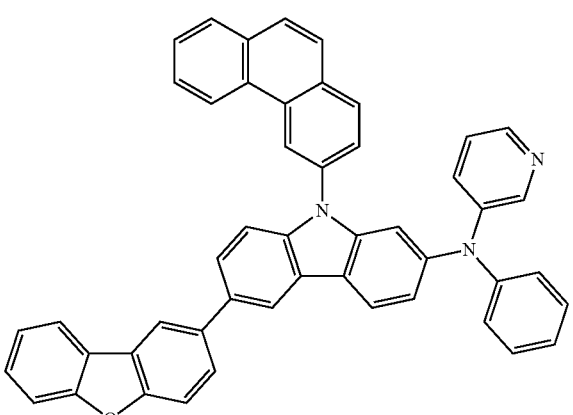
2-25
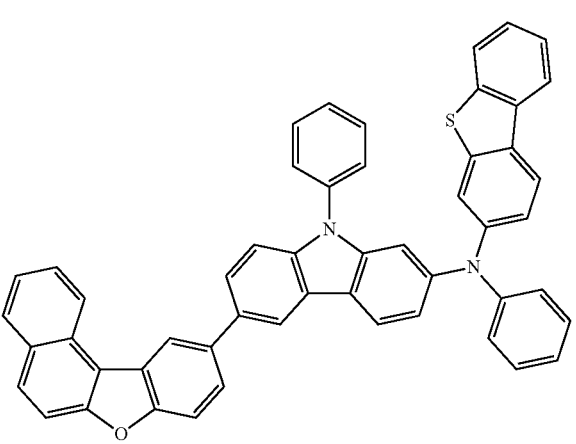
2-26
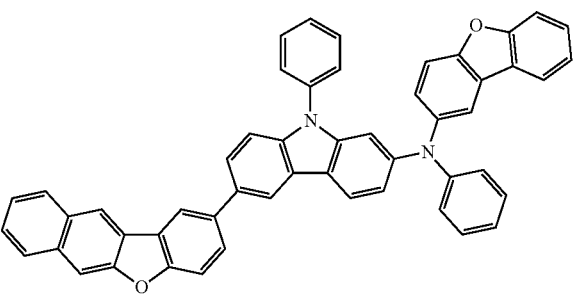
2-27
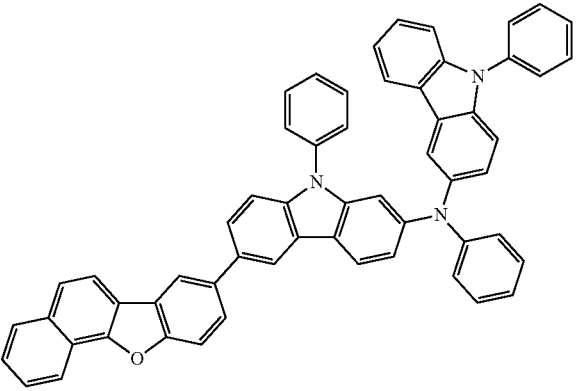

2-28

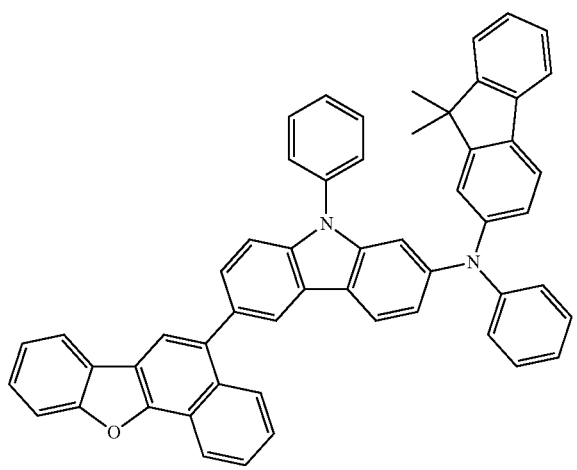

2-31

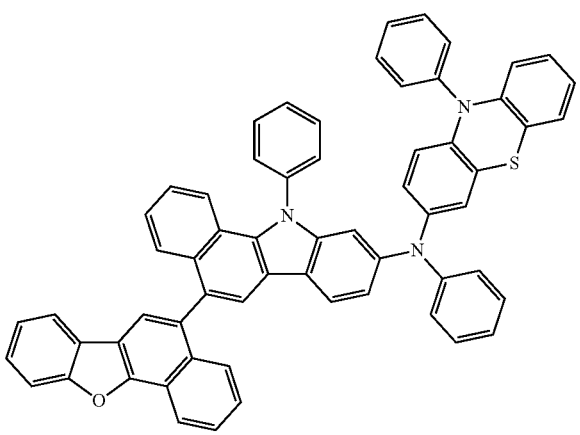

2-29

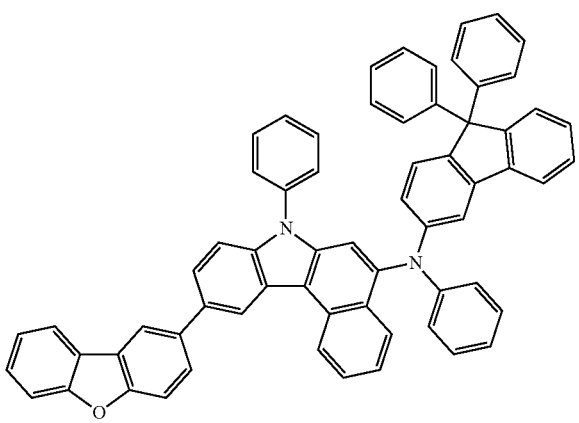

2-32

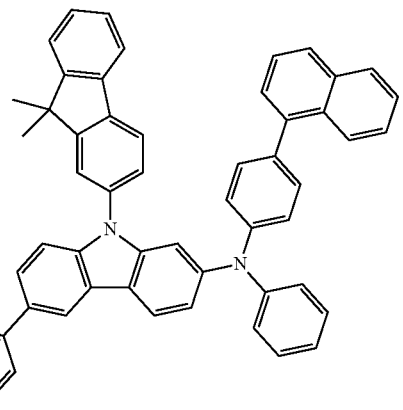

2-30

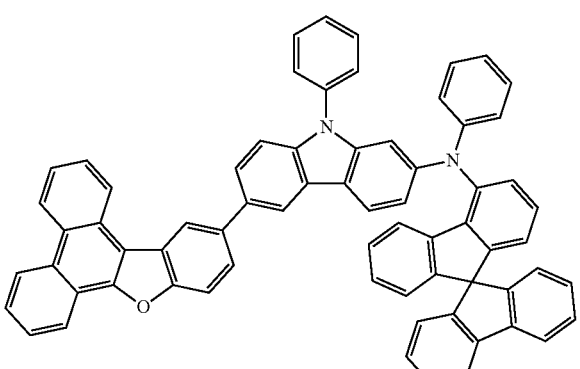

In another aspect of the present invention, the present invention provides an organic electric element comprising a first electrode, a second electrode, and an organic material layer formed between the first electrode and the second electrode, wherein the organic material layer may comprise at least one layer of a hole injection layer, a hole transport layer, an emission-auxiliary layer, a light emitting layer, an electron transport layer, an electron transport auxiliary layer and an electron injection layer, and the above compound is comprised in at least one layer of the organic material layer. The compound comprised in the organic material layer may be comprised as a single compound or as the component of the mixture of two or more kinds. That is, the compound represented by the formula 1 may be used as material of a hole injection layer, a hole transport layer, an emission-auxiliary layer, a light emitting layer, an electron transport layer, an electron transport auxiliary layer or/and an electron injection layer. Preferably, the compound may be used as material of a hole transport layer or/and an emission-auxiliary layer.

In another aspect of the present invention, the present invention provides an organic electric element further comprising a layer for improving luminous efficiency formed on at least one side of sides of the first electrode and the second electrode, wherein at least one side is not facing the organic material layer.

Further, the organic material layer may be formed by any one of the processes of spin coating, nozzle printing, inkjet printing, slot coating, dip coating or roll-to-roll.

In another aspect of the present invention, the present invention provides an electronic device comprising a display device and a control unit for driving the display device, wherein the display device comprises the organic electric element. Here, the organic electric element may be an organic light emitting diode, an organic solar cell, an organic photo conductor, an organic transistor, or an element for monochromatic or white illumination.

Hereinafter, Synthesis method of the compound represented by Formula 1 and preparation method of an organic electric element according to one embodiment of the present invention will be described in detail by way of examples. However, the present invention is not limited to the following examples.

SYNTHESIS EXAMPLE

For example, as shown in Reaction Scheme 1 below, the compounds (final products) according to the present invention can be synthesized by reacting Sub 1 with Sub 2, but there is no limitation thereto.

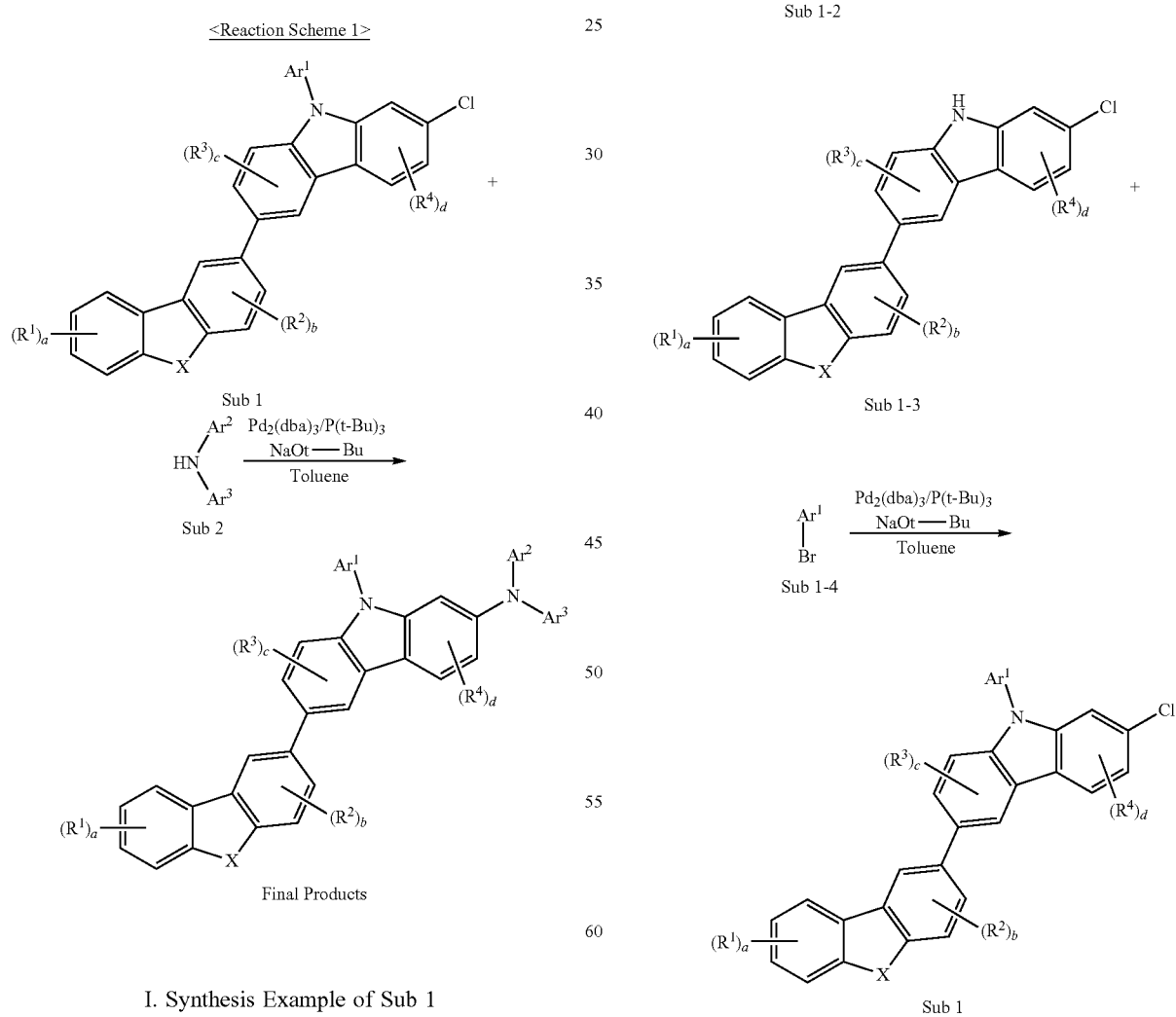

I. Synthesis Example of Sub 1

Sub 1 of the Reaction Scheme 1 can be synthesized according to the reaction route of the following Reaction Scheme 2, but there is no limitation thereto.

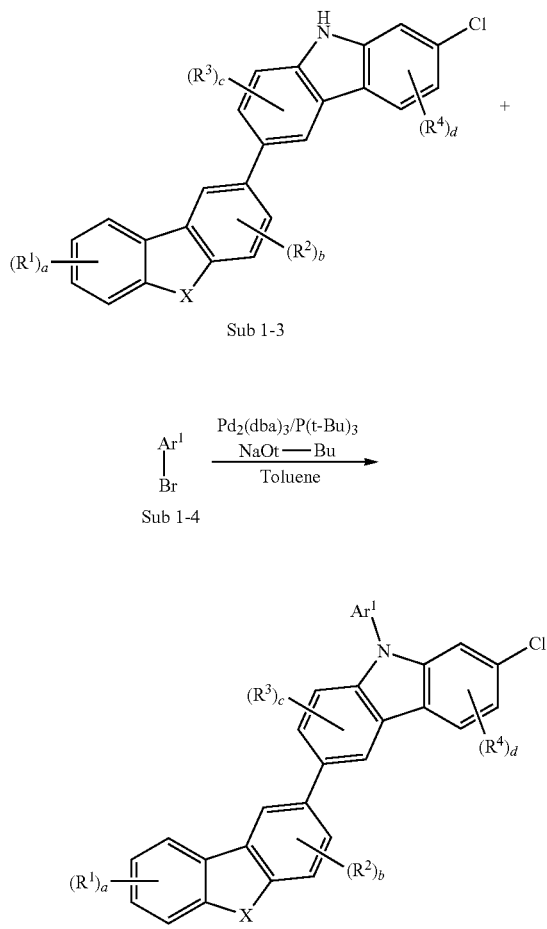

Synthesis examples of the compounds belonging to Sub 1 are as follows.

Synthesis Example of Sub 1(1)

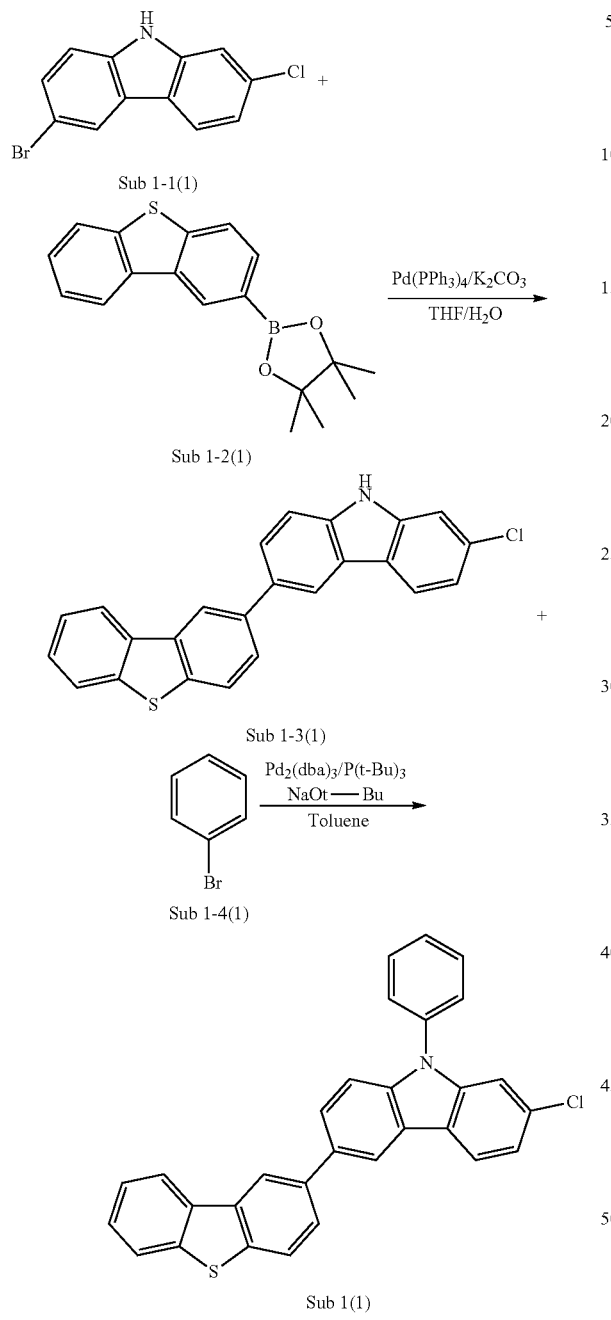

Synthesis Method of Sub 1-3(1)

After Sub 1-1(1) (30.9 g, 0.11 mol), Sub 1-2(1) (40.3 g, 0.13 mol), K$_2$CO$_3$ (46.03 g, 0.33 mol), Pd(PPh$_3$)$_4$ (5.13 g, 4 mol %) were dissolved in THF and a small amount of water, the mixture was refluxed for 12 hours. When the reaction was completed, the reaction product was cooled to room temperature, and then extracted with CH$_2$Cl$_2$ and water. Then, the organic layer was dried with MgSO$_4$ and concentrated. Then, the concentrate was applied to silica gel column to obtain Sub 1-3(1) 31.2 g (yield: 74%) of the product.

Synthesis Method of Sub 1(1) After Sub 1-3(1) (18.2 g, 47.3 mmol) was dissolved in toluene (500 mL) in a round bottom flask, Sub 1-4(1) (8.2 g, 52.0 mmol), Pd$_2$(dba)$_3$ (2.2 g, 2.4 mmol), P(t-Bu)$_3$ (1 g, 4.73 mmol), NaOt-Bu (13.6 g, 141.8 mmol) were added the solution, and then the mixture was stirred at 100□. When the reaction was completed, the reaction product was extracted with CH$_2$Cl$_2$ and water, and then the organic layer was dried with MgSO$_4$ and concentrated. Then, the concentrate was applied to silica gel column and recrystallized to obtain 17.4 g (yield: 80%) of the product.

Synthesis Example of Sub 1(8)

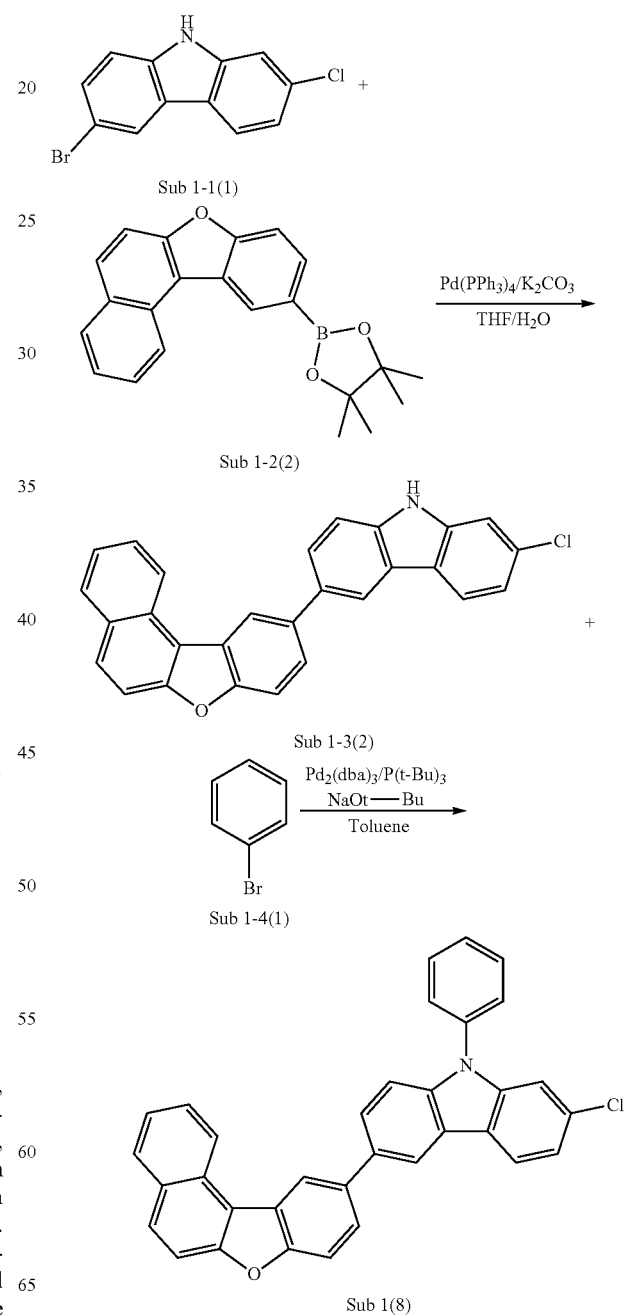

Synthesis Method of Sub 1-3(2)

Sub 1-3(2) 34.9 g (yield: 76%) of the product was obtained by reacting Sub 1-1(1) (30.9 g, 0.11 mol) and Sub 1-2(2) (44.7 g, 0.13 mol) by the same method as in synthesis of Sub 1-3(1).

Synthesis Method of Sub 1(8)

Sub 1-3(2) (19.8 g, 47.3 mmol) was dissolved in toluene (500 mL) in a round bottom flask, then 19.2 g (yield: 82%) of the product was obtained by reacting the solution and Sub 1-4(1) (8.2 g, 52.0 mmol) by the same method as in synthesis of Sub 1(1).

The compounds belonging to Sub 1 may be, but not limited to, the following compounds, and Table 1 shows FD-MS (Field Desorption-Mass Spectrometry) values of them.

Sub 1(1)

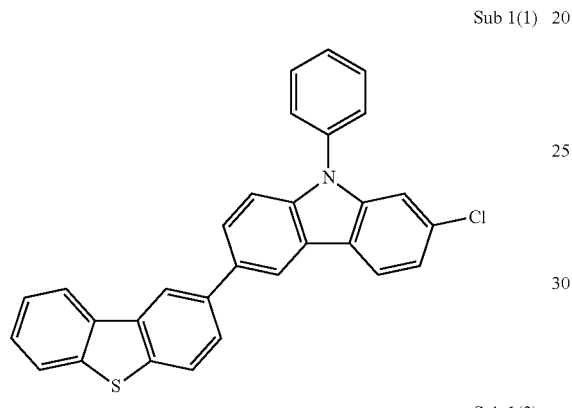

Sub 1(2)

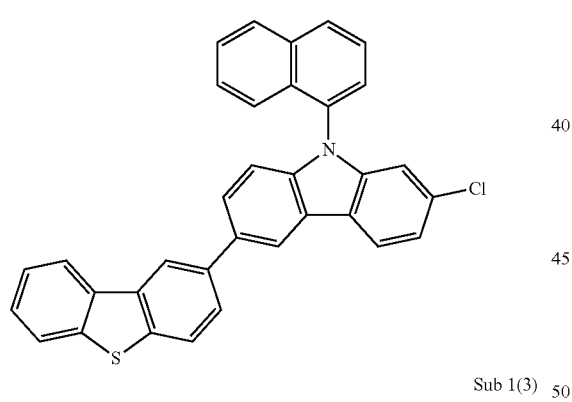

Sub 1(3)

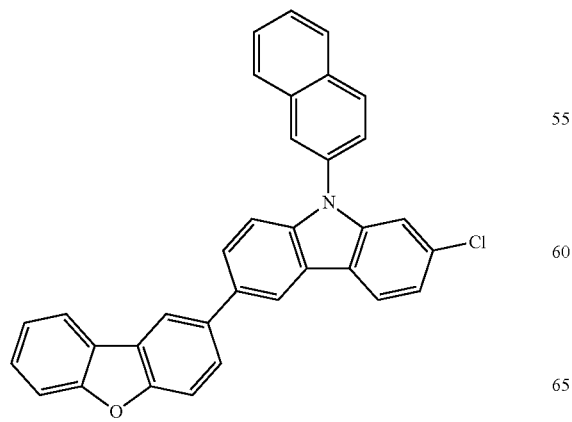

Sub 1(4)

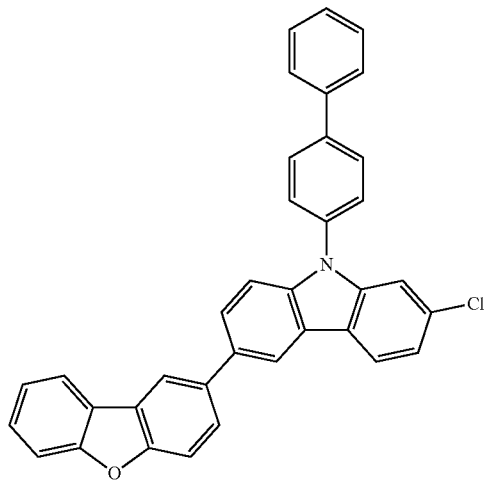

Sub 1(5)

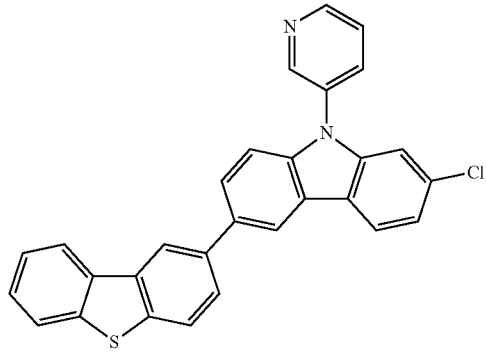

Sub 1(6)

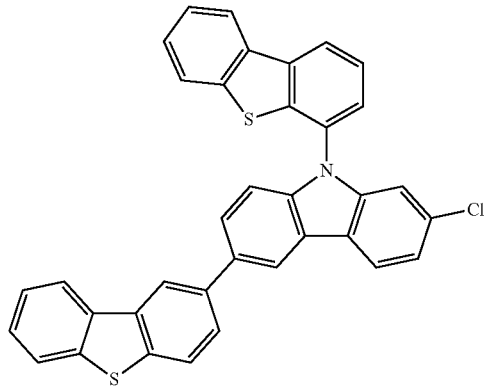

Sub 1(7)
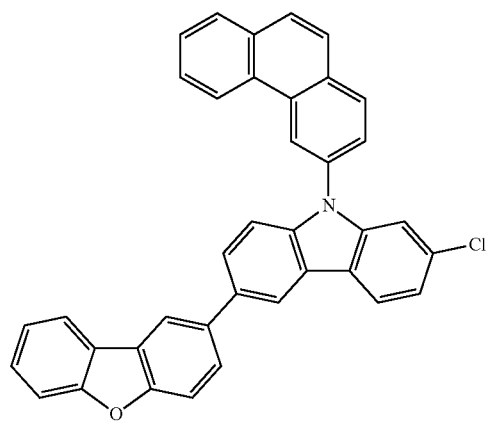
Sub 1(8)
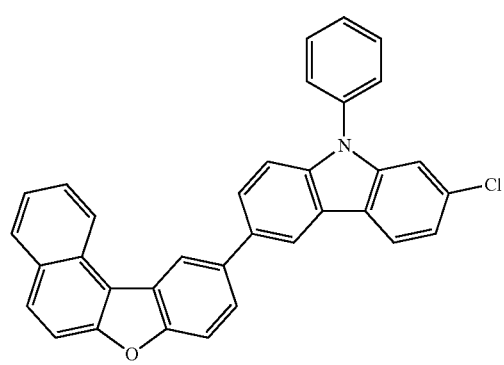
Sub 1(9)
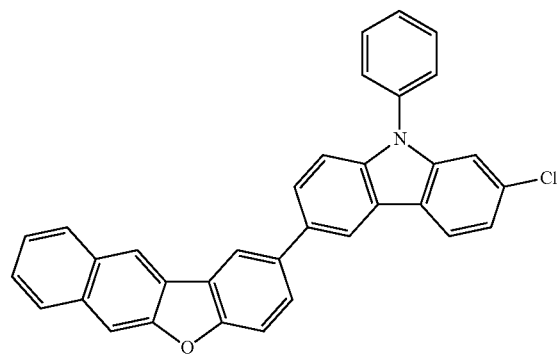
Sub 1(10)
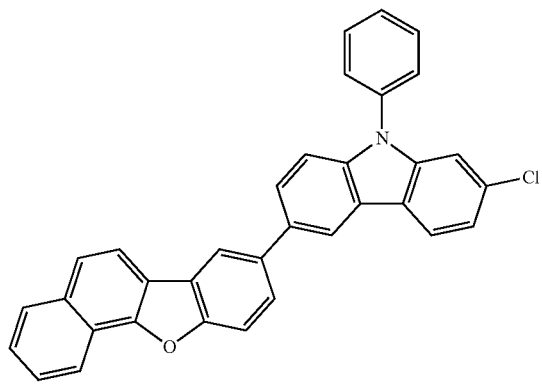
Sub 1(11)
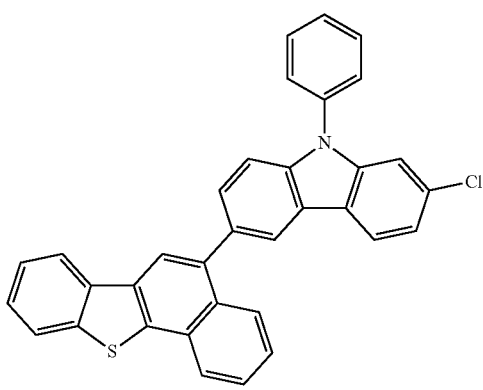
Sub 1(12)
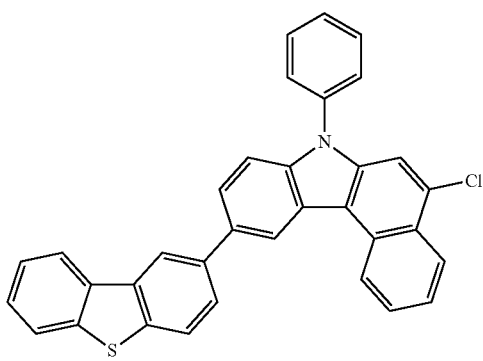
Sub 1(13)
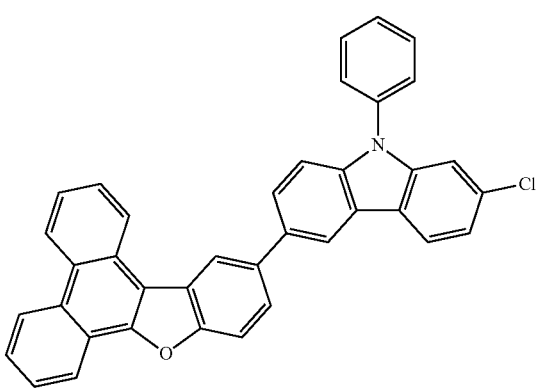
Sub 1(14)
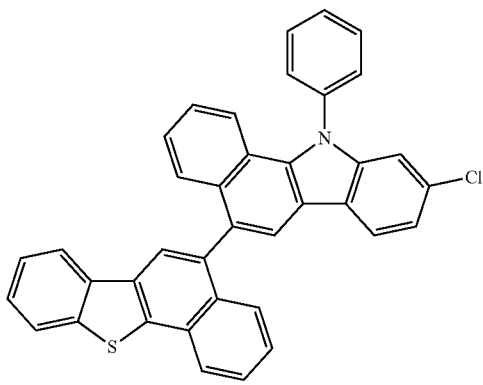

39 -continued

Sub 1(15)

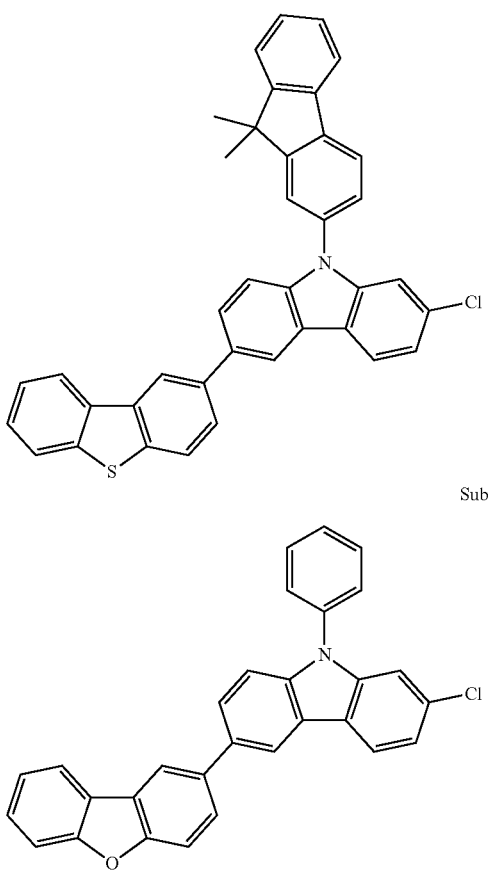

Sub 1(16)

Synthesis Example of Sub 2-1

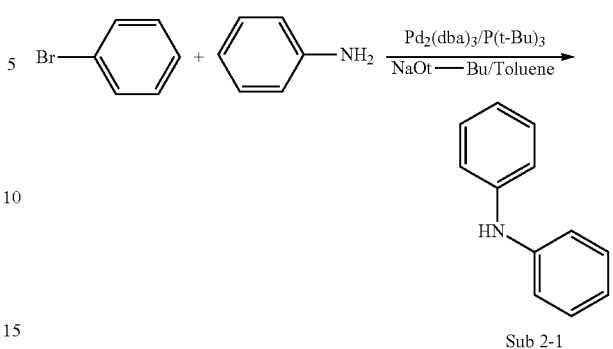

Sub 2-1

After bromobenzene (37.1 g, 236.2 mmol) was dissolved in toluene (2200 mL) in a round bottom flask, aniline (20 g, 214.8 mmol), $Pd_2(dba)_3$ (9.83 g, 10.7 mmol), $P(t-Bu)_3$ (4.34 g, 21.5 mmol), NaOt-Bu (62 g, 644.3 mmol) were added thereto and the mixture was stirred at 100□. When the reaction was completed, the reaction product was extracted with ether and water, and then, the organic layer was dried with $MgSO_4$ and concentrated. Then, the concentrate was applied to silica gel column and recrystallized to obtain 28 g (yield: 77%) of the product.

Synthesis Example of Sub 2-13

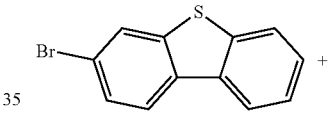

+

TABLE 1

| Compound | FD-MS | Compound | FD-MS |
|---|---|---|---|
| Sub 1(1) | m/z = 459.08($C_{30}H_{18}ClNS$ = 459.99) | Sub 1(2) | m/z = 509.10($C_{34}H_{20}ClNS$ = 510.05) |
| Sub 1(3) | m/z = 509.10($C_{34}H_{20}ClNS$ = 510.05) | Sub 1(4) | m/z = 519.14($C_{36}H_{22}ClNO$ = 520.03) |
| Sub 1(5) | m/z = 460.08($C_{29}H_{17}ClN_2S$ = 460.98) | Sub 1(6) | m/z = 565.07($C_{36}H_{20}ClNS_2$ = 566.13) |
| Sub 1(7) | m/z = 543.14($C_{38}H_{22}ClNO$ = 544.05) | Sub 1(8) | m/z = 493.12($C_{34}H_{20}ClNO$ = 493.99) |
| Sub 1(9) | m/z = 493.12($C_{34}H_{20}ClNO$ = 493.99) | Sub 1(10) | m/z = 493.12($C_{34}H_{20}ClNO$ = 493.99) |
| Sub 1(11) | m/z = 509.10($C_{34}H_{20}ClNS$ = 510.05) | Sub 1(12) | m/z = 509.10($C_{34}H_{20}ClNS$ = 510.05) |
| Sub 1(13) | m/z = 543.14($C_{38}H_{22}ClNO$ = 544.05) | Sub 1(14) | m/z = 559.12($C_{38}H_{22}ClNS$ = 560.11) |
| Sub 1(15) | m/z = 575.15($C_{39}H_{26}ClNS$ = 576.15) | Sub 1(16) | m/z = 443.11($C_{30}H_{18}ClNO$ = 443.93) |

II. Synthesis Example of Sub 2

Sub 2 of the Reaction Scheme 1 can be synthesized according to the reaction route of the following Reaction Scheme 3, but there is no limitation thereto.

<Reaction Scheme 3>

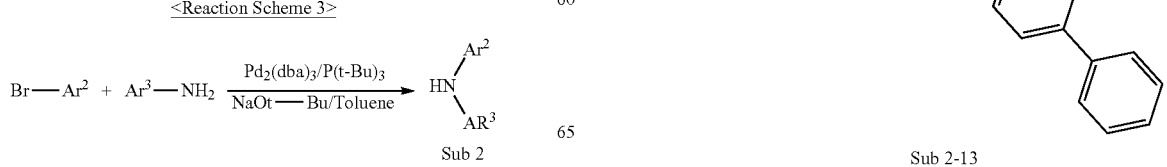

Sub 2-13

37.9 g (yield: 73%) of the product was obtained by reacting 3-bromodibenzo[b,d]thiophene (42.8 g, 162.5 mmol), toluene(1550 mL), [1,1'-biphenyl]-4-amine (25 g, 147.7 mmol), Pd₂(dba)₃ (6.76 g, 162.5 mmol), P(t-Bu)₃ (3 g, 14.8 mmol) and NaOt-Bu (42.6 g, 443.2 mmol) by the same method as in synthesis of Sub 2-1.
The compounds belonging to Sub 2 may be, but not limited to, the following compounds, and Table 2 shows FD-MS values of them.
Sub 2-1
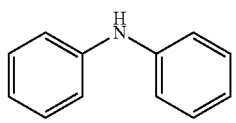
Sub 2-2
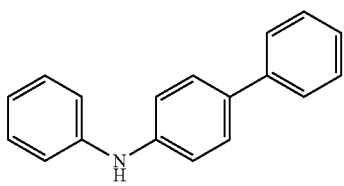
Sub 2-3
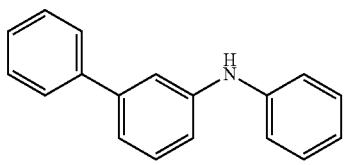
Sub 2-4
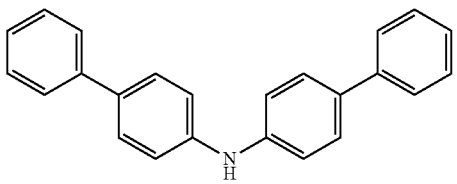
Sub 2-5
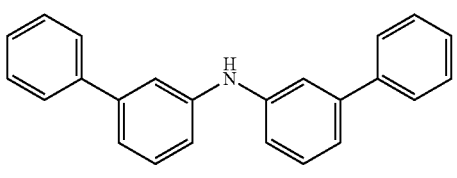
Sub 2-6
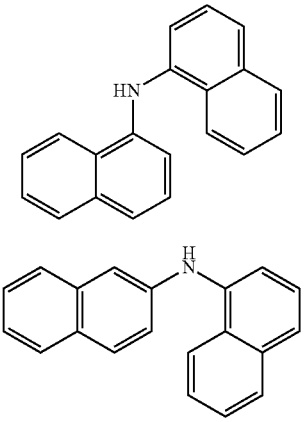
Sub 2-7
Sub 2-8
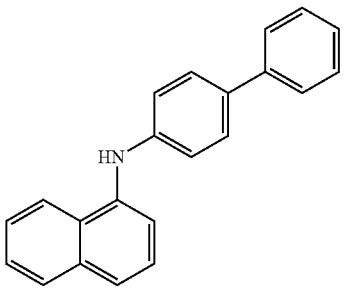
Sub 2-9
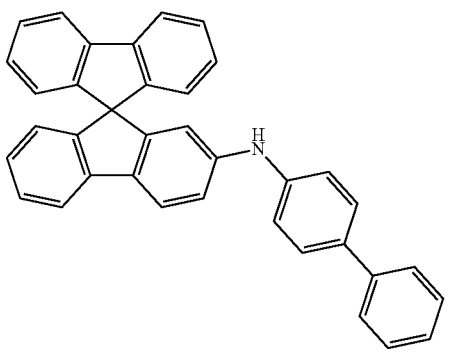
Sub 2-10
Sub 2-11
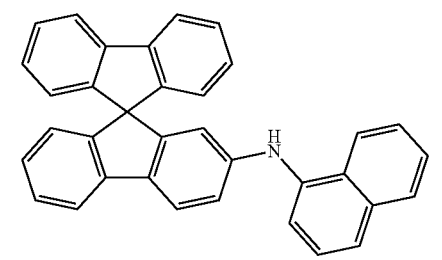
Sub 2-12
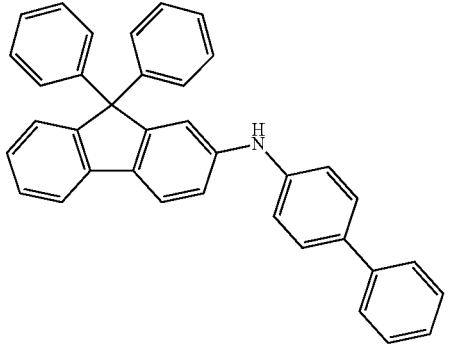

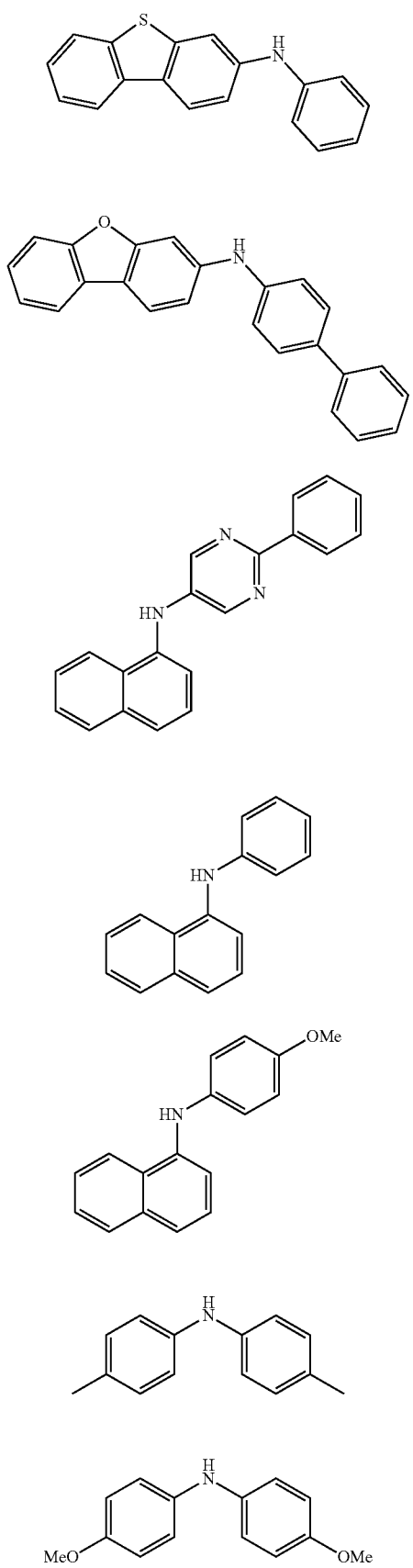
Sub 2-13
Sub 2-14
Sub 2-15
Sub 2-16
Sub 2-17
Sub 2-18
Sub 2-19
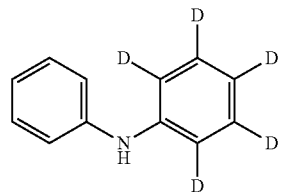
Sub 2-20
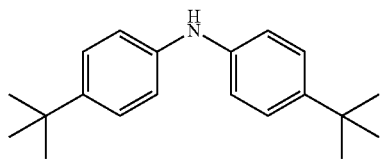
Sub 2-21
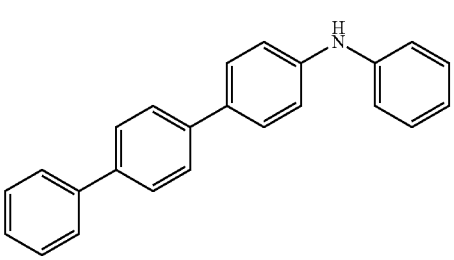
Sub 2-22
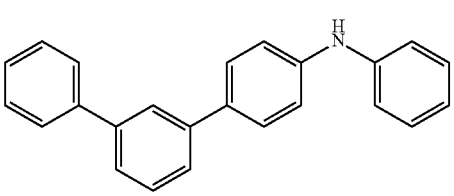
Sub 2-23
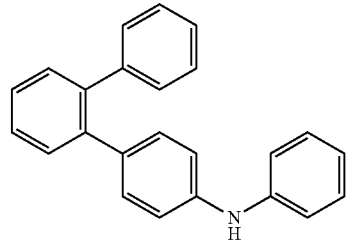
Sub 2-24
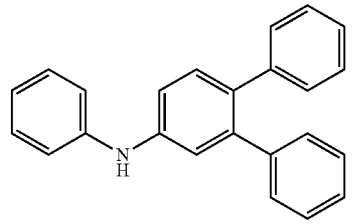
Sub 2-25
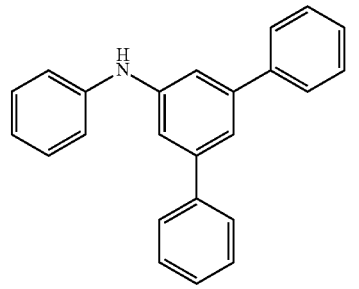
Sub 2-26

Sub 2-27
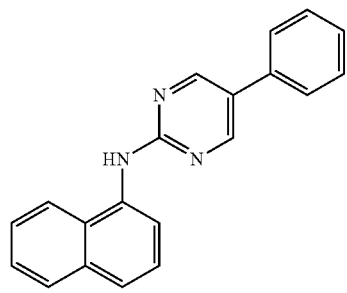
Sub 2-28
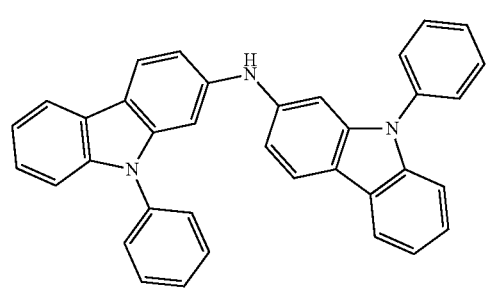
Sub 2-29
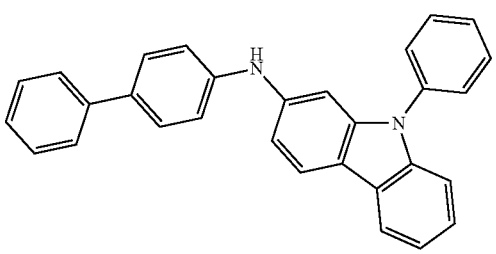
Sub 2-30
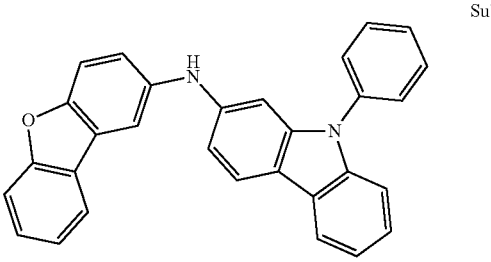
Sub 2-31
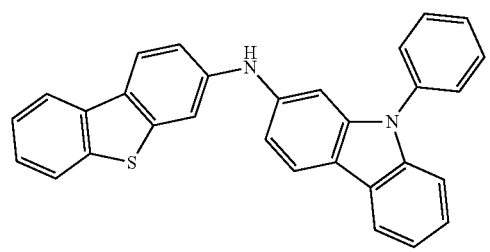
Sub 2-32
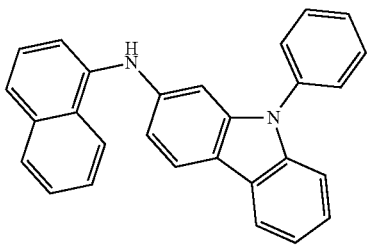
Sub 2-33
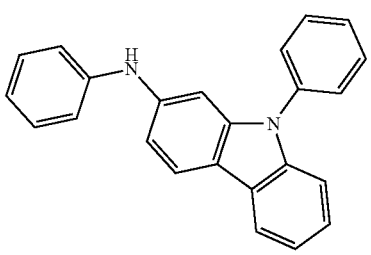
Sub 2-34
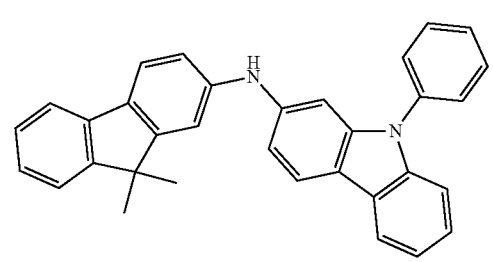
Sub 2-35
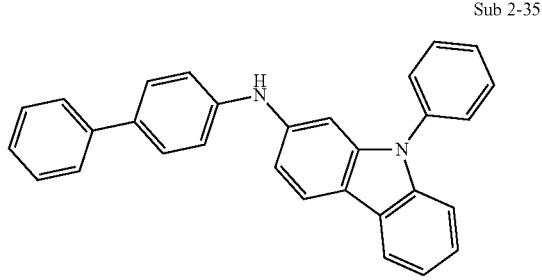
Sub 2-36
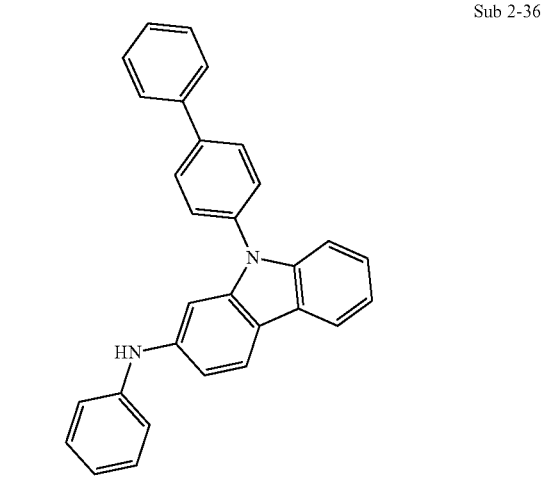

Sub 2-37
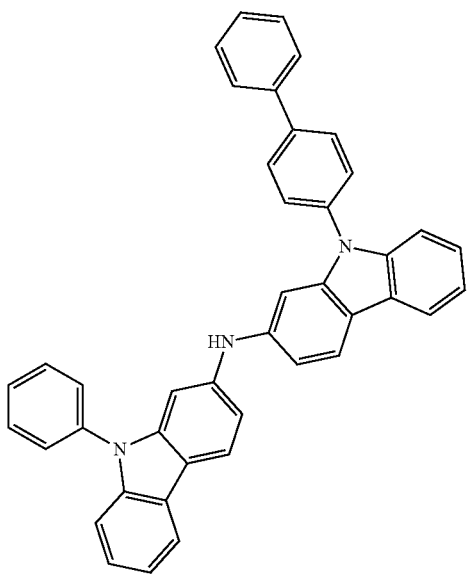
Sub 2-38
Sub 2-39
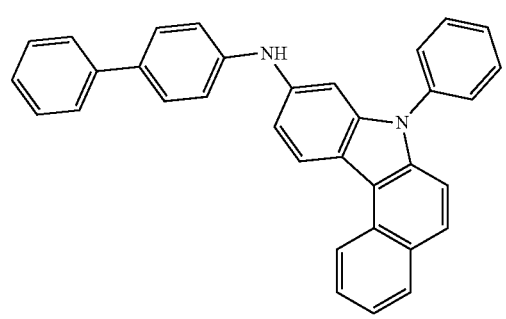
Sub 2-40
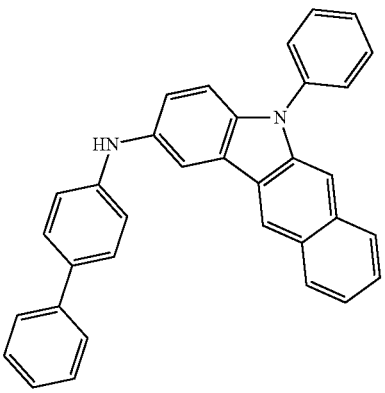
Sub 2-41
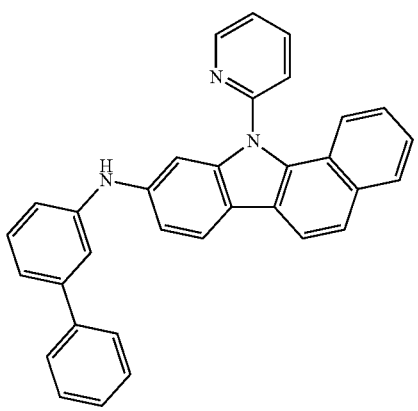
Sub 2-42
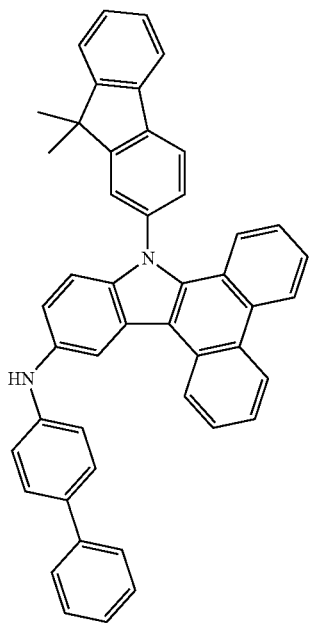

Sub 2-43

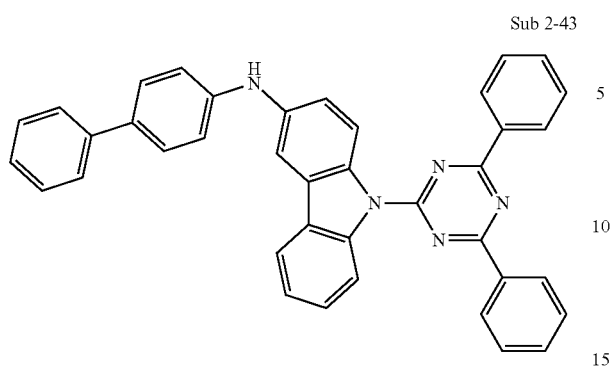

Sub 2-45

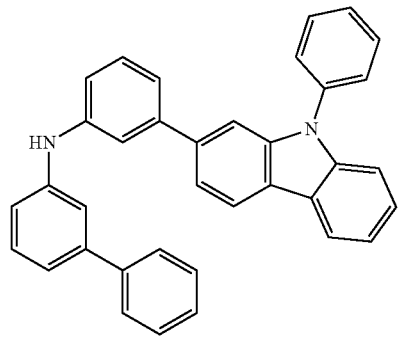

Sub 2-44

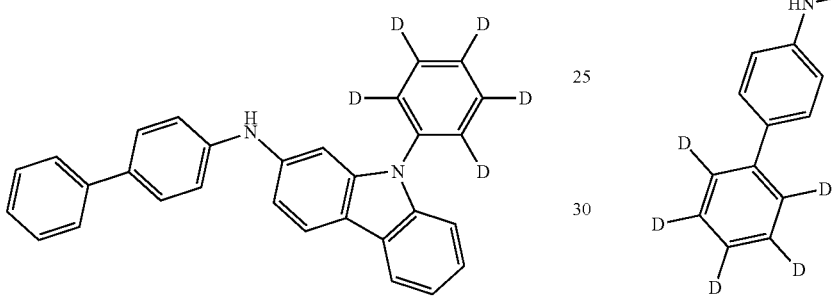

Sub 2-46

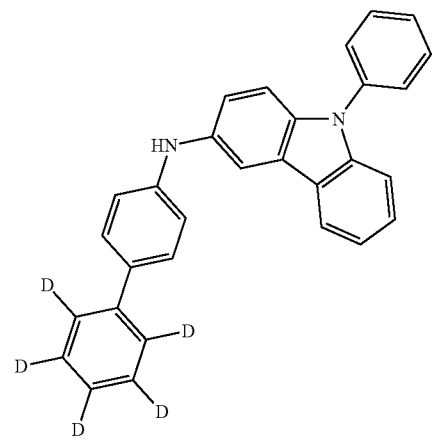

TABLE 2

| Compound | FD-MS | Compound | FD-MS |
| --- | --- | --- | --- |
| Sub 2-1 | m/z = 169.09($C_{12}H_{11}N$ = 169.22) | Sub 2-2 | m/z = 245.12($C_{18}H_{15}N$ = 245.32) |
| Sub 2-3 | m/z = 245.12($C_{18}H_{15}N$ = 245.32) | Sub 2-4 | m/z = 321.15($C_{24}H_{19}N$ = 321.41) |
| Sub 2-5 | m/z = 321.15 ($C_{24}H_{19}N$ = 321.41) | Sub 2-6 | m/z = 269.12($C_{20}H_{15}N$ = 269.34) |
| Sub 2-7 | m/z = 269.12($C_{20}H_{15}N$ = 269.34) | Sub 2-8 | m/z = 295.14($C_{22}H_{17}N$ = 295.38) |
| Sub 2-9 | m/z = 409.18($C_{31}H_{23}N$ = 409.52) | Sub 2-10 | m/z = 483.20($C_{37}H_{25}N$ = 483.60) |
| Sub 2-11 | m/z = 459.20($C_{35}H_{25}N$ = 459.58) | Sub 2-12 | m/z = 485.21($C_{37}H_{27}N$ = 485.62) |
| Sub 2-13 | m/z = 275.08($C_{18}H_{13}NS$ = 275.37) | Sub 2-14 | m/z = 335.13($C_{24}H_{17}NO$ = 335.40) |
| Sub 2-15 | m/z = 297.13($C_{20}H_{15}N_3$ = 297.35) | Sub 2-16 | m/z = 219.10($C_{16}H_{13}N$ = 219.28) |
| Sub 2-17 | m/z = 249.12($C_{17}H_{15}NO$ = 249.31) | Sub 2-18 | m/z = 197.12($C_{14}H_{15}N$ = 197.28) |
| Sub 2-19 | m/z = 229.11($C_{14}H_{15}NO_2$ = 229.27) | Sub 2-20 | m/z = 174.12($C_{12}H_6D_5N$ = 174.25) |
| Sub 2-21 | m/z = 281.21($C_{20}H_{27}N$ = 281.44) | Sub 2-22 | m/z = 321.15($C_{24}H_{19}N$ = 321.41) |
| Sub 2-23 | m/z = 321.15($C_{24}H_{19}N$ = 321.41) | Sub 2-24 | m/z = 321.15($C_{24}H_{19}N$ = 321.41) |
| Sub 2-25 | m/z = 321.15($C_{24}H_{19}N$ = 321.41) | Sub 2-26 | m/z = 321.15($C_{24}H_{19}N$ = 321.41) |
| Sub 2-27 | m/z = 297.13($C_{20}H_{15}N_3$ = 297.35) | Sub 2-28 | m/z = 499.20($C_{36}H_{25}N_3$ = 499.60) |
| Sub 2-29 | m/z = 499.20($C_{36}H_{22}N_2$ = 410.51) | Sub 2-30 | m/z = 424.16($C_{30}H_{20}N_2O$ = 424.49) |
| Sub 2-31 | m/z = 440.13($C_{30}H_{20}N_2S$ = 440.56) | Sub 2-32 | m/z = 384.16($C_{28}H_{20}N_2$ = 384.47) |
| Sub 2-33 | m/z = 334.15($C_{24}H_{18}N_2$ = 334.41) | Sub 2-34 | m/z = 450.21($C_{33}H_{26}N_2$ = 450.57) |
| Sub 2-35 | m/z = 410.18($C_{30}H_{22}N_2$ = 410.51) | Sub 2-36 | m/z = 410.18($C_{30}H_{22}N_2$ = 410.51) |
| Sub 2-37 | m/z = 575.24($C_{42}H_{29}N_3$ = 575.70) | Sub 2-38 | m/z = 574.24($C_{43}H_{30}N_2$ = 574.71) |
| Sub 2-39 | m/z = 460.19($C_{34}H_{24}N_2$ = 460.57) | Sub 2-40 | m/z = 460.19($C_{34}H_{24}N_2$ = 460.57) |
| Sub 2-41 | m/z = 461.19($C_{33}H_{23}N_3$ = 461.56) | Sub 2-42 | m/z = 626.27($C_{47}H_{34}N_2$ = 626.79) |
| Sub 2-43 | m/z = 565.23($C_{39}H_{27}N_5$ = 565.67) | Sub 2-44 | m/z = 415.21($C_{30}H_{17}D_5N_2$ = 415.54) |
| Sub 2-45 | m/z = 486.21($C_{36}H_{26}N_2$ = 486.61) | Sub 2-46 | m/z = 415.21($C_{30}H_{17}D_5N_2$ = 415.54) |

III. Synthesis Examples of Final Products

Synthesis Example of 1-1

Synthesis Example of 1-25

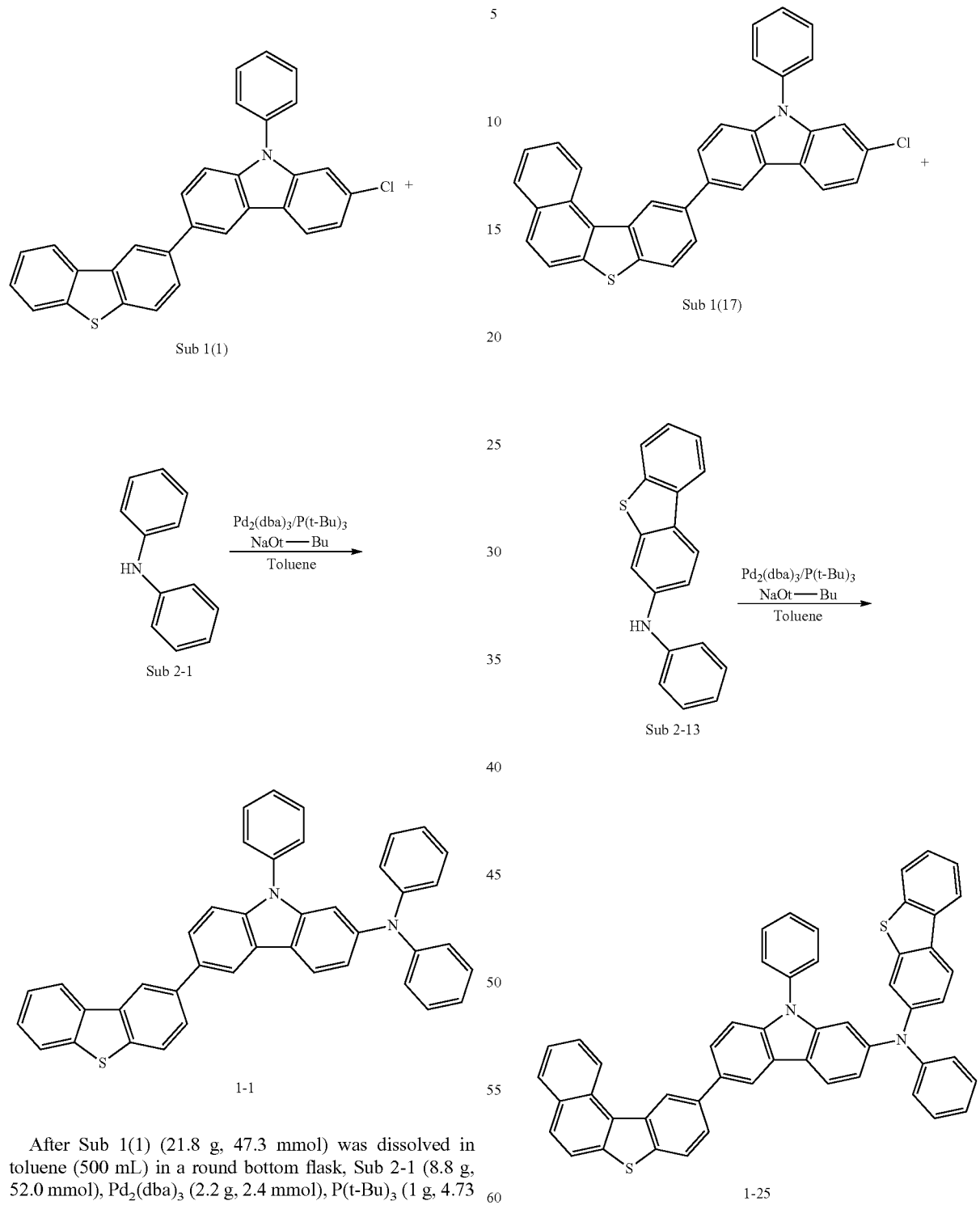

After Sub 1(1) (21.8 g, 47.3 mmol) was dissolved in toluene (500 mL) in a round bottom flask, Sub 2-1 (8.8 g, 52.0 mmol), Pd$_2$(dba)$_3$ (2.2 g, 2.4 mmol), P(t-Bu)$_3$ (1 g, 4.73 mmol), NaOt-Bu (13.6 g, 141.8 mmol) were added the solution and the mixture was stirred at 100□. When the reaction was completed, the reaction product was extracted with CH$_2$Cl$_2$ and water, and then, the organic layer was dried with MgSO$_4$ and concentrated. Then, the concentrate was applied to silica gel column and recrystallized to obtain 23.6 g (yield: 84%) of the product.

After Sub 1(17) (24.1 g, 47.3 mmol) was dissolved in toluene (500 mL) in a round bottom flask, Sub 2-13 (14.3 g, 52.0 mmol) was added to the solution, and then 28.0 g (yield: 79%) of the product was obtained by the same method as in synthesis of the compound 1-1.

Synthesis Example of 1-32
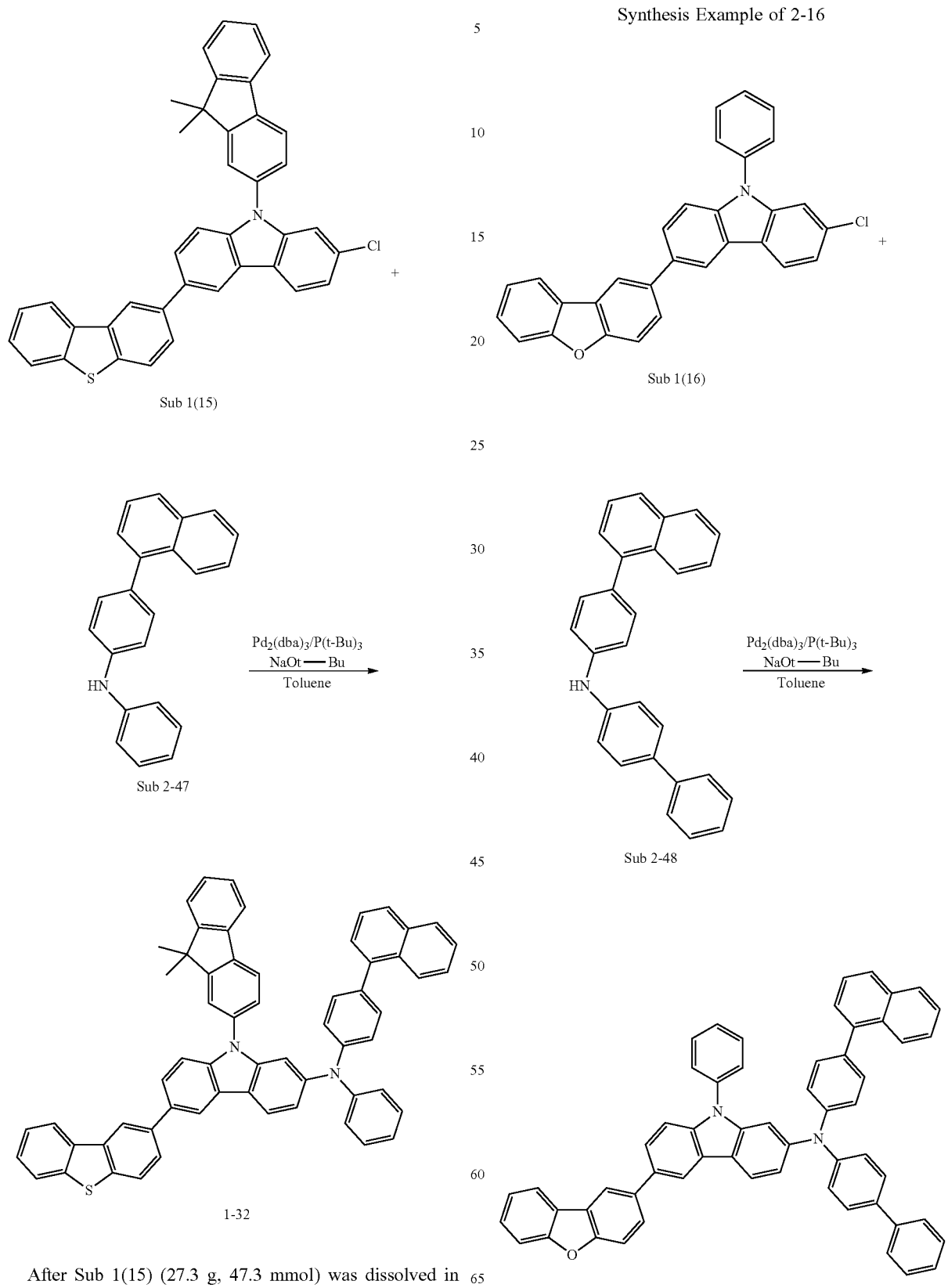
Synthesis Example of 2-16
After Sub 1(15) (27.3 g, 47.3 mmol) was dissolved in toluene (500 mL) in a round bottom flask, Sub 2-47 (15.4 g, 52.0 mmol) was added to the solution, and then 32.0 g (yield: 81%) of the product was obtained by the same method as in synthesis of the compound 1-1.

After Sub 1(16) (21.0 g, 47.3 mmol) was dissolved in toluene (500 mL) in a round bottom flask, Sub 2-48 (19.3 g, 52.0 mmol) was added to the solution, and then 30.6 g (yield: 83%) of the product was obtained by the same method as in synthesis of the compound 1-1.

Synthesis Example of 2-21

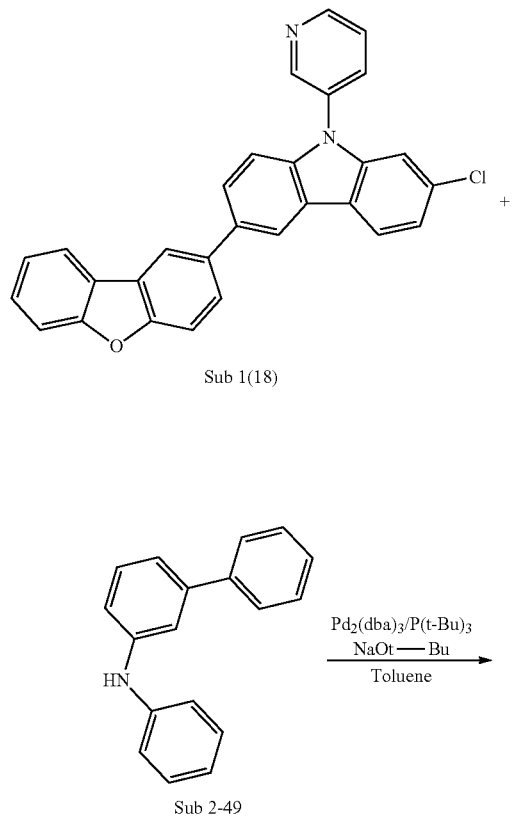

After Sub 1(18) (21.0 g, 47.3 mmol) was dissolved in toluene (500 mL) in a round bottom flask, Sub 2-49 (12.8 g, 52.0 mmol) was added to the solution, and then 23.8 g (yield: 77%) of the product was obtained by the same method as in synthesis of the compound 1-1.

Synthesis Example of 2-31

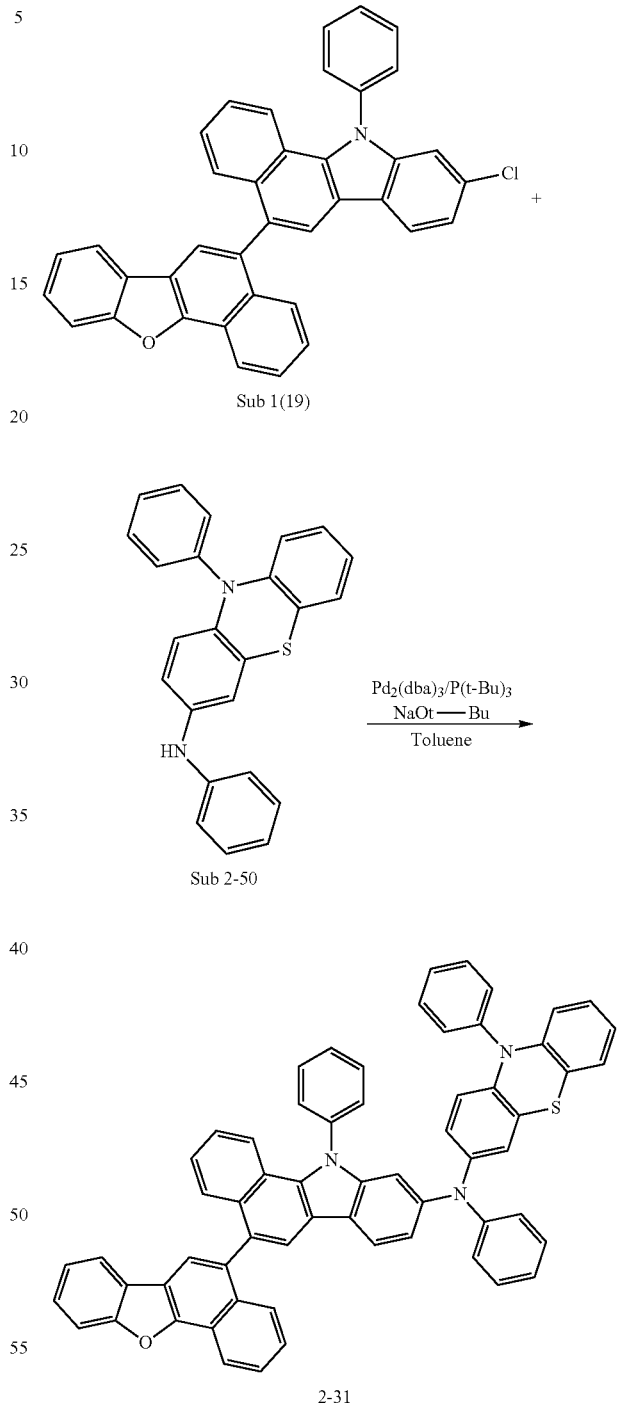

After Sub 1(19) (25.7 g, 47.3 mmol) was dissolved in toluene (500 mL) in a round bottom flask, Sub 2-50 (19.1 g, 52.0 mmol) was added to the solution, and then 30.6 g (yield: 74%) of the product was obtained by the same method as in synthesis of the compound 1-1.

The FD-MS values of the compounds of the present invention prepared according to the above synthesis examples are shown in Table 3 below.

TABLE 3

| Compound | FD-MS | Compound | FD-MS |
|---|---|---|---|
| 1-1 | m/z = 592.20($C_{42}H_{28}N_2S$ = 592.76) | 1-2 | m/z = 642.21($C_{46}H_{30}N_2S$ = 642.82) |
| 1-3 | m/z = 642.21($C_{46}H_{30}N_2S$ = 642.82) | 1-4 | m/z = 668.23($C_{48}H_{32}N_2S$ = 668.86) |
| 1-5 | m/z = 718.24($C_{52}H_{34}N_2S$ = 718.92) | 1-6 | m/z = 794.28($C_{58}H_{38}N_2S$ = 795.02) |
| 1-7 | m/z = 742.24($C_{54}H_{34}N_2S$ = 742.94) | 1-8 | m/z = 643.21($C_{45}H_{29}N_3S$ = 643.81) |
| 1-9 | m/z = 748.20($C_{52}H_{32}N_2S_2$ = 748.96) | 1-10 | m/z = 732.22($C_{52}H_{32}N_2OS$ = 732.90) |
| 1-11 | m/z = 807.27($C_{58}H_{37}N_3S$ = 808.02) | 1-12 | m/z = 758.28($C_{55}H_{38}N_2S$ = 758.98) |
| 1-13 | m/z = 908.32($C_{67}H_{44}N_2S$ = 909.16) | 1-14 | m/z = 906.31($C_{67}H_{42}N_2S$ = 907.15) |
| 1-15 | m/z = 865.26($C_{60}H_{39}N_3S_2$ = 866.11) | 1-16 | m/z = 794.28($C_{58}H_{38}N_2S$ = 795.02) |
| 1-17 | m/z = 642.21($C_{46}H_{30}N_2S$ = 642.82) | 1-18 | m/z = 692.23$C_{50}H_{32}N_2S$ = 692.88) |
| 1-19 | m/z = 718.24($C_{52}H_{34}N_2S$ = 718.92) | 1-20 | m/z = 744.26($C_{54}H_{36}N_2S$ = 744.96) |
| 1-21 | m/z = 669.22($C_{47}H_{31}N_3S$ = 669.85) | 1-22 | m/z = 850.25($C_{60}H_{38}N_2S_2$ = 851.10) |
| 1-23 | m/z = 692.23($C_{50}H_{32}N_2S$ = 692.88) | 1-24 | m/z = 693.22($C_{49}H_{31}N_3S$ = 693.87) |
| 1-25 | m/z = 748.20($C_{52}H_{32}N_2S_2$ = 748.96) | 1-26 | m/z = 732.22($C_{52}H_{32}N_2OS$ = 732.90) |
| 1-27 | m/z = 807.27($C_{58}H_{37}N_3S$ = 808.02) | 1-28 | m/z = 758.28($C_{55}H_{38}N_2S$ = 758.98) |
| 1-29 | m/z = 882.31($C_{65}H_{42}N_2S$ = 883.13) | 1-30 | m/z = 930.31($C_{69}H_{42}N_2S$ = 931.17) |
| 1-31 | m/z = 889.26($C_{62}H_{39}N_3S_2$ = 890.14) | 1-32 | m/z = 834.31($C_{61}H_{48}N_2S$ = 835.08) |
| 2-1 | m/z = 576.22($C_{42}H_{28}N_2O$ = 576.70) | 2-2 | m/z = 626.24($C_{46}H_{30}N_2O$ = 626.76) |
| 2-3 | m/z = 626.24($C_{46}H_{30}N_2O$ = 626.76) | 2-4 | m/z = 652.25($C_{48}H_{32}N_2O$ = 652.80) |
| 2-5 | m/z = 702.27($C_{52}H_{34}N_2O$ = 702.86) | 2-6 | m/z = 778.30($C_{58}H_{38}N_2O$ = 778.96) |
| 2-7 | m/z = 762.27($C_{54}H_{34}N_2O$ = 726.88) | 2-8 | m/z = 627.23($C_{45}H_{29}N_3O$ = 627.75) |
| 2-9 | m/z = 732.22($C_{52}H_{32}N_2OS$ = 732.90) | 2-10 | m/z = 716.25($C_{52}H_{32}N_2O_2$ = 716.84) |
| 2-11 | m/z = 791.29($C_{58}H_{37}N_3O$ = 791.95) | 2-12 | m/z = 742.30($C_{55}H_{38}N_2O$ = 742.92) |
| 2-13 | m/z = 892.35($C_{67}H_{44}N_2O$ = 893.10) | 2-14 | m/z = 890.33($C_{67}H_{42}N_2O$ = 891.09) |
| 2-15 | m/z = 849.28($C_{60}H_{39}N_3OS$ = 850.05) | 2-16 | m/z = 778.30($C_{58}H_{38}N_2O$ = 778.96) |
| 2-17 | m/z = 626.24($C_{46}H_{30}N_2O$ = 626.76) | 2-18 | m/z = 767.25$C_{50}H_{32}N_2O$ = 676.82) |
| 2-19 | m/z = 702.27($C_{52}H_{34}N_2O$ = 702.86) | 2-20 | m/z = 728.28($C_{54}H_{36}N_2O$ = 728.90) |
| 2-21 | m/z = 653.25($C_{47}H_{31}N_3O$ = 653.79) | 2-22 | m/z = 834.27($C_{60}H_{38}N_2OS$ = 835.04) |
| 2-23 | m/z = 676.25($C_{50}H_{32}N_2O$ = 676.82) | 2-24 | m/z = 677.25($C_{49}H_{31}N_3O$ = 677.81) |
| 2-25 | m/z = 732.22($C_{52}H_{32}N_2OS$ = 732.90) | 2-26 | m/z = 716.25($C_{52}H_{32}N_2O_2$ = 716.84) |
| 2-27 | m/z = 791.29($C_{58}H_{37}N_3O$ = 791.95) | 2-28 | m/z = 742.30($C_{55}H_{38}N_2O$ = 742.92) |
| 2-29 | m/z = 866.33($C_{65}H_{42}N_2O$ = 867.06) | 2-30 | m/z = 914.33($C_{69}H_{42}N_2O$ = 915.11) |
| 2-31 | m/z = 873.28($C_{62}H_{39}N_3OS$ = 874.07) | 2-32 | m/z = 818.33($C_{61}H_{48}N_2O$ = 819.02) |

Fabrication and Evaluation of Organic Electronic Element

[Example 1] Red OLED (an Emission-Auxiliary Layer)

A film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer formed on a glass substrate to form a hole injection layer with a thickness of 60 nm. Subsequently, N,N'-Bis(1-naphthalenyl)-N,N'-bis-phenyl-(1,1'-biphenyl)-4,4'-diamine (hereinafter, "NPB") was vacuum-deposited with a thickness of 60 nm on the hole injection layer to form a hole transport layer.

Subsequently, a film of the compound 1-1 of the present invention was vacuum-deposited on the hole transport layer to form a emission-auxiliary layer with a thickness of 20 nm. A light emitting layer with a thickness of 30 nm was deposited on the emission-auxiliary layer by using 4,4'-N,N'-dicarbazole-biphenyl (hereinafter, "CBP") as a host material and bis-(1-phenylisoquinoline)iridium(III)acetylacetonate (hereinafter, "(piq)$_2$Ir(acac)") as a opant material in a weight ratio of 95:5.

Next, a film of (1,1'-biphenyl-4-olato)bis(2-methyl-8-quinolinolato)aluminum (hereinafter, "BAlq") was vacuum-deposited with a thickness of 10 nm on the light emitting layer to form a hole blocking layer, and a film of tris-(8-hydroxyquinoline)aluminum (hereinafter, "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 64] Red OLED (an Emission-Auxiliary Layer)

The OLEDs were fabricated in the same manner as described in Example 1 except that the compounds of the present invention described in the following Table 4, instead of the compound 1-1 of the present invention, were used as an emission-auxiliary layer material.

Comparative Example 1

The OLED was fabricated in the same manner as described in Example 1 except that an emission-auxiliary layer was not formed.

[Comparative Example 2] to [Comparative Example 5]

The OLEDs were fabricated in the same manner as described in Example 1 except that the Comparative compounds A to D, instead of the compound 1-1 of the present invention, were used as an emission-auxiliary layer material.

<Comp.compd A>

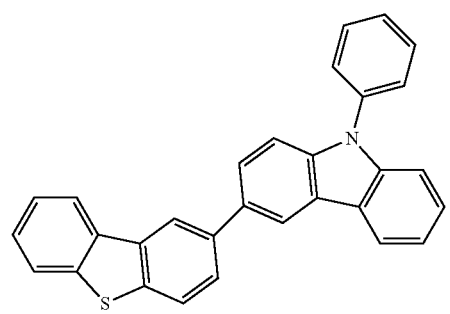

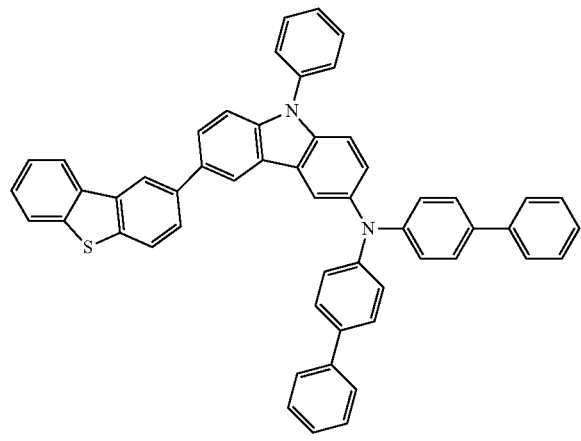
<Comp.compd B>

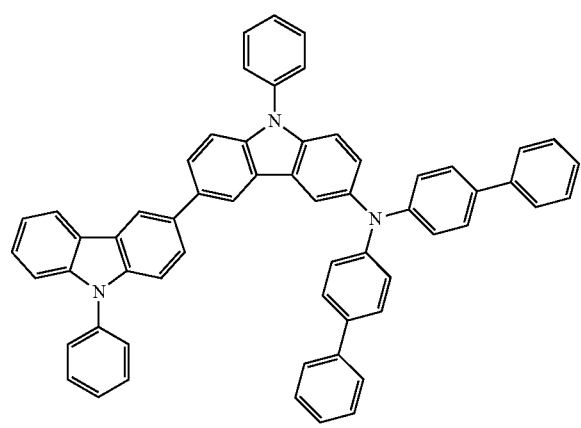
<Comp.compd C>

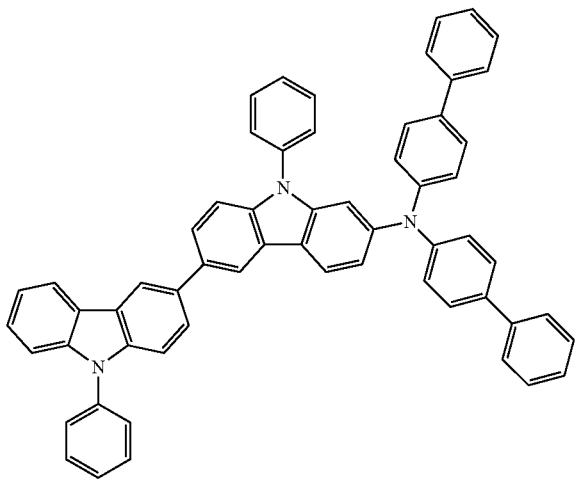
<Comp.compd D>

Electroluminescence (EL) characteristics were measured with a PR-650(Photoresearch) by applying a forward bias DC voltage to the OLEDs prepared in Examples 1 to 64 of the present invention and Comparative Examples 1 to 5. And, the T95 life time was measured using a life time measuring apparatus manufactured by Macscience Inc. at reference brightness of 2500 cd/m$^2$. The measurement results are shown in Tables 4 below.

TABLE 4

|   | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| comp.Ex(1) | — | 6.0 | 32.9 | 2500.0 | 7.6 | 61.8 | (0.66, 0.32) |
| comp.Ex(2) | comp.Com A | 6.3 | 23.1 | 2500.0 | 10.8 | 74.5 | (0.67, 0.32) |
| comp.Ex(3) | comp.Com B | 5.7 | 12.6 | 2500.0 | 19.8 | 107.6 | (0.66, 0.35) |
| comp.Ex(4) | comp.Com C | 5.9 | 15.7 | 2500.0 | 15.9 | 90.3 | (0.66, 0.35) |
| comp.Ex(4) | comp.Com D | 5.8 | 14.2 | 2500.0 | 17.6 | 98.9 | (0.66, 0.35) |
| Ex.(1) | Com.(1-1) | 5.1 | 9.3 | 2500.0 | 26.8 | 121.9 | (0.66, 0.32) |
| Ex.(2) | Com.(1-2) | 5.2 | 9.8 | 2500.0 | 25.5 | 124.4 | (0.66, 0.35) |
| Ex.(3) | Com.(1-3) | 5.3 | 9.6 | 2500.0 | 25.9 | 123.1 | (0.66, 0.35) |
| Ex.(4) | Com.(1-4) | 5.2 | 9.2 | 2500.0 | 27.1 | 124.9 | (0.65, 0.35) |
| Ex.(5) | Com.(1-5) | 5.1 | 9.9 | 2500.0 | 25.2 | 122.8 | (0.65, 0.35) |
| Ex.(6) | Com.(1-6) | 5.1 | 9.7 | 2500.0 | 25.8 | 121.5 | (0.66, 0.35) |
| Ex.(7) | Com.(1-7) | 5.1 | 9.3 | 2500.0 | 26.8 | 121.1 | (0.66, 0.35) |
| Ex.(8) | Com.(1-8) | 5.2 | 10.0 | 2500.0 | 25.1 | 123.4 | (0.66, 0.35) |
| Ex.(9) | Com.(1-9) | 5.2 | 9.5 | 2500.0 | 26.2 | 123.2 | (0.66, 0.35) |
| Ex.(10) | Com.(1-10) | 5.2 | 10.0 | 2500.0 | 25.0 | 124.5 | (0.66, 0.35) |
| Ex.(11) | Com.(1-11) | 5.2 | 9.7 | 2500.0 | 25.8 | 123.4 | (0.66, 0.35) |
| Ex.(12) | Com.(1-12) | 5.1 | 9.8 | 2500.0 | 25.6 | 122.4 | (0.66, 0.35) |
| Ex.(13) | Com.(1-13) | 5.1 | 9.0 | 2500.0 | 27.7 | 122.6 | (0.66, 0.35) |
| Ex.(14) | Com.(1-14) | 5.3 | 9.5 | 2500.0 | 26.2 | 123.7 | (0.66, 0.35) |
| Ex.(15) | Com.(1-15) | 5.2 | 9.5 | 2500.0 | 26.3 | 120.5 | (0.66, 0.35) |
| Ex.(16) | Com.(1-16) | 5.2 | 9.9 | 2500.0 | 25.4 | 123.4 | (0.66, 0.35) |
| Ex.(17) | Com.(1-17) | 5.2 | 9.5 | 2500.0 | 26.3 | 120.9 | (0.66, 0.35) |
| Ex.(18) | Com.(1-18) | 5.1 | 10.0 | 2500.0 | 25.1 | 120.1 | (0.66, 0.35) |
| Ex.(19) | Com.(1-19) | 5.3 | 9.0 | 2500.0 | 27.8 | 123.8 | (0.66, 0.35) |
| Ex.(20) | Com.(1-20) | 5.2 | 9.6 | 2500.0 | 26.0 | 120.2 | (0.66, 0.35) |
| Ex.(21) | Com.(1-21) | 5.2 | 9.0 | 2500.0 | 27.9 | 122.2 | (0.66, 0.35) |
| Ex.(22) | Com.(1-22) | 5.1 | 9.0 | 2500.0 | 27.7 | 124.4 | (0.66, 0.35) |
| Ex.(23) | Com.(1-23) | 5.2 | 9.2 | 2500.0 | 27.2 | 121.9 | (0.66, 0.35) |
| Ex.(24) | Com.(1-24) | 5.1 | 9.0 | 2500.0 | 27.7 | 124.8 | (0.66, 0.35) |

TABLE 4-continued

|  | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex.(25) | Com.(1-25) | 5.3 | 9.1 | 2500.0 | 27.4 | 122.4 | (0.66, 0.35) |
| Ex.(26) | Com.(1-26) | 5.2 | 9.5 | 2500.0 | 26.3 | 122.5 | (0.66, 0.35) |
| Ex.(27) | Com.(1-27) | 5.1 | 9.3 | 2500.0 | 27.0 | 124.9 | (0.66, 0.35) |
| Ex.(28) | Com.(1-28) | 5.1 | 9.3 | 2500.0 | 26.8 | 124.6 | (0.66, 0.35) |
| Ex.(29) | Com.(1-29) | 5.2 | 9.8 | 2500.0 | 25.5 | 123.6 | (0.66, 0.35) |
| Ex.(30) | Com.(1-30) | 5.2 | 9.6 | 2500.0 | 25.9 | 120.6 | (0.66, 0.35) |
| Ex.(31) | Com.(1-31) | 5.2 | 9.2 | 2500.0 | 27.1 | 122.1 | (0.66, 0.35) |
| Ex.(32) | Com.(1-32) | 5.1 | 9.9 | 2500.0 | 25.2 | 124.4 | (0.66, 0.35) |
| Ex.(33) | Com.(2-1) | 5.4 | 10.2 | 2500.0 | 24.5 | 116.7 | (0.66, 0.35) |
| Ex.(34) | Com.(2-2) | 5.4 | 10.6 | 2500.0 | 23.6 | 115.3 | (0.66, 0.35) |
| Ex.(35) | Com.(2-3) | 5.4 | 10.3 | 2500.0 | 24.2 | 116.2 | (0.66, 0.35) |
| Ex.(36) | Com.(2-4) | 5.4 | 10.7 | 2500.0 | 23.3 | 118.6 | (0.66, 0.35) |
| Ex.(37) | Com.(2-5) | 5.4 | 10.8 | 2500.0 | 23.1 | 116.3 | (0.66, 0.35) |
| Ex.(38) | Com.(2-6) | 5.5 | 10.4 | 2500.0 | 24.1 | 116.4 | (0.66, 0.35) |
| Ex.(39) | Com.(2-7) | 5.4 | 10.8 | 2500.0 | 23.2 | 118.3 | (0.66, 0.35) |
| Ex.(40) | Com.(2-8) | 5.5 | 10.4 | 2500.0 | 24.1 | 116.5 | (0.66, 0.35) |
| Ex.(41) | Com.(2-9) | 5.5 | 10.6 | 2500.0 | 23.6 | 116.8 | (0.66, 0.35) |
| Ex.(42) | Com.(2-10) | 5.4 | 10.6 | 2500.0 | 23.6 | 116.3 | (0.66, 0.35) |
| Ex.(43) | Com.(2-11) | 5.4 | 10.3 | 2500.0 | 24.2 | 116.7 | (0.66, 0.35) |
| Ex.(44) | Com.(2-12) | 5.5 | 10.4 | 2500.0 | 24.2 | 117.1 | (0.66, 0.35) |
| Ex.(45) | Com.(2-13) | 5.5 | 10.0 | 2500.0 | 25.0 | 120.0 | (0.66, 0.35) |
| Ex.(46) | Com.(2-14) | 5.4 | 10.8 | 2500.0 | 23.2 | 115.9 | (0.66, 0.35) |
| Ex.(47) | Com.(2-15) | 5.5 | 10.5 | 2500.0 | 23.9 | 119.8 | (0.66, 0.32) |
| Ex.(48) | Com.(2-16) | 5.4 | 10.4 | 2500.0 | 24.1 | 117.5 | (0.67, 0.32) |
| Ex.(49) | Com.(2-17) | 5.5 | 10.0 | 2500.0 | 25.0 | 117.0 | (0.66, 0.32) |
| Ex.(50) | Com.(2-18) | 5.5 | 10.6 | 2500.0 | 23.5 | 116.5 | (0.66, 0.35) |
| Ex.(51) | Com.(2-19) | 5.5 | 10.8 | 2500.0 | 23.1 | 115.1 | (0.66, 0.35) |
| Ex.(52) | Com.(2-20) | 5.4 | 10.8 | 2500.0 | 23.1 | 115.3 | (0.65, 0.35) |
| Ex.(53) | Com.(2-21) | 5.4 | 10.6 | 2500.0 | 23.5 | 118.5 | (0.65, 0.35) |
| Ex.(54) | Com.(2-22) | 5.5 | 10.1 | 2500.0 | 24.7 | 116.8 | (0.66, 0.32) |
| Ex.(55) | Com.(2-23) | 5.4 | 10.1 | 2500.0 | 24.6 | 116.3 | (0.67, 0.32) |
| Ex.(56) | Com.(2-24) | 5.5 | 10.7 | 2500.0 | 23.3 | 119.2 | (0.66, 0.35) |
| Ex.(57) | Com.(2-25) | 5.5 | 10.6 | 2500.0 | 23.5 | 118.6 | (0.66, 0.35) |
| Ex.(58) | Com.(2-26) | 5.4 | 10.7 | 2500.0 | 23.4 | 117.6 | (0.66, 0.32) |
| Ex.(59) | Com.(2-27) | 5.4 | 10.9 | 2500.0 | 23.0 | 116.5 | (0.66, 0.35) |
| Ex.(60) | Com.(2-28) | 5.5 | 10.3 | 2500.0 | 24.2 | 116.0 | (0.66, 0.35) |
| Ex.(61) | Com.(2-29) | 5.5 | 10.2 | 2500.0 | 24.6 | 118.4 | (0.65, 0.35) |
| Ex.(62) | Com.(2-30) | 5.4 | 10.3 | 2500.0 | 24.4 | 116.1 | (0.65, 0.35) |
| Ex.(63) | Com.(2-31) | 5.4 | 10.3 | 2500.0 | 24.4 | 117.8 | (0.66, 0.35) |
| Ex.(64) | Com.(2-32) | 5.4 | 10.9 | 2500.0 | 23.0 | 115.2 | (0.66, 0.35) |

From the results shown in Table 4, it can be seen that the driving voltage is lowered and the luminous efficiency and lifetime of the organic electroluminescent device are remarkably improved when compounds of the present invention were used as an emission-auxiliary layer material, compared with those of an organic electroluminescent device not comprising an emission-auxiliary layer or the organic electroluminescent device of Comparative Examples using Comparatives A to D as material of an emission-auxiliary layer.

That is, the device results of Comparative Examples 2 to 5 using Comparative Compounds A to D as the material of an emission-auxiliary layer were superior to those of Comparative Example 1 in which an emission-auxiliary layer was not formed, and Examples 1 to 64, in which the compound of the present invention was used as a material for an emission-auxiliary layer, exhibited the best device results, wherein the compound of the present invention is similar to the comparative compound but a specific substituent such as dibenzothiophene is necessarily substituted and the amine group is substituted at the 2-position of the carbazole.

Comparing the results of Comparative Compounds A to C, it was confirmed that Comparative Example 2 using Comparative Compound A in which amine group was not substituted showed better efficiency and lifetime than Comparative Example 1 in which an emission-auxiliary layer was not formed, and the driving voltage of Comparative Example 2 was slightly increased. On the other hand, it is confirmed that On the other hand, Comparative Compounds B and C substituted with an amine group showed an improvement in not only efficiency and lifetime but also driving voltage as compared with Comparative Example 1.

Comparing the results of the compounds of the comparative compounds C and D, or the comparative compound B and the compounds of the present invention, the differences according to the substitution positions of the amine groups can be explained.

It can be seen that the comparative compound D or the compound of the present invention, which has the same substituent as the compounds B or C substituted with an amine group at the 3-position of the carbazole hut substituted with an amine group at the 2-position of the carbazole, has the deeper HOMO value and the faster hole injection and migration mobility.

Therefore, it is considered that as the hole injection and migration ability is improved, the deterioration of the ITO and HTL interface is reduced to improve the lifetime of the device and as more holes move to the light emitting layer, the charge balance in the light emitting layer of holes and electrons increases, so that light emission is well performed in the light emitting layer rather than at the interface of the hole transporting layer, as a result, the driving voltage, efficiency and lifetime are maximized.

In addition, it is considered that the LUMO energy of 3-carbazole and 2-carbazole is also different, and the conjugation length of 2-carbazole is shorter than that of 3-carbazole, so that 2-carbazole has a high T1 value and the ability to block electrons is also improved. This suggests that the properties of compounds such as HOMO, LUMO, and T1 are changed depending on the position of the substitution even if the core and substituent are same, and this may serve as a major factor in improving the performance of the device, resulting in different results.

In addition, comparing the results of the compounds of the comparative compounds C and D, or the comparative compound B and the compounds of the present invention, the difference between when dibenzothiophene or dibenzofuran is substituted and when carbazole is substituted can be seen.

It can be confirmed that the device results of the compound substituted with dibenzothiophene or dibenzofuran are superior to those of the compound substituted with carbazole (Comparative Examples 3 vs. 4 or Comparative Example 5 vs. Examples 1 to 64). It is considered that this is because dibenzothiophene or dibenzofuran have higher refractive indexes and Tg values than carbazole, and therefore, efficiency and thermal stability are improved when the device deposited, and these differences result in significantly improved results. That is, it suggests that even though dibenzothiophene, dibenzofurane and carbazole are belong to the same category of heterocycles, the properties of them are quite different, and therefore the result of a significantly different device can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:
1. A compound of Formula 1:

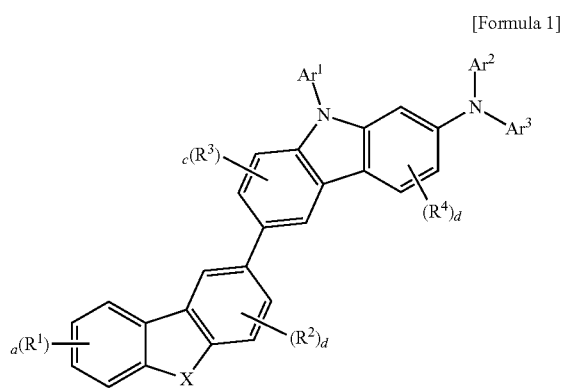

[Formula 1]

wherein:

X is O or S, $R^1$ to $R^4$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), and neighboring $R^1$ groups, neighboring $R^2$ groups, neighboring $R^3$ groups, or neighboring $R^4$ groups are optionally linked to each other to form a ring, a is an integer of 0 to 4, and b, c and d are each an integer of 0 to 3, and when each of a, b, c and d is an integer of 2 or more, each of the plurality of $R^1$s to $R^4$s may be the same or different from each other, $Ar^1$ to $Ar^3$ are each independently selected from the group consisting of a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group and -L'-N($R_a$)($R_b$), with the proviso that where $Ar_1$ is the heterocyclic group, $Ar^1$ is not $C_8$-$C_9$-heterocyclic group, L' is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, $R_a$ and $R_b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P, and the above aryl group, fluorenyl group, heterocyclic group, fused ring group, alkyl group, alkenyl group, alkynyl group, alkoxyl group, aryloxy group, arylene group and fluorenylene group are each optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

2. The compound of claim 1, wherein Formula 1 is represented by the following Formula 2 or 3:

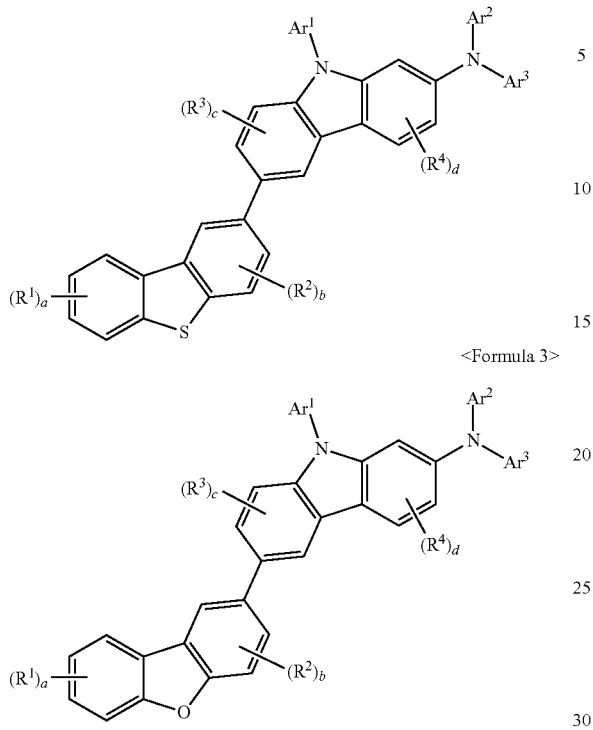
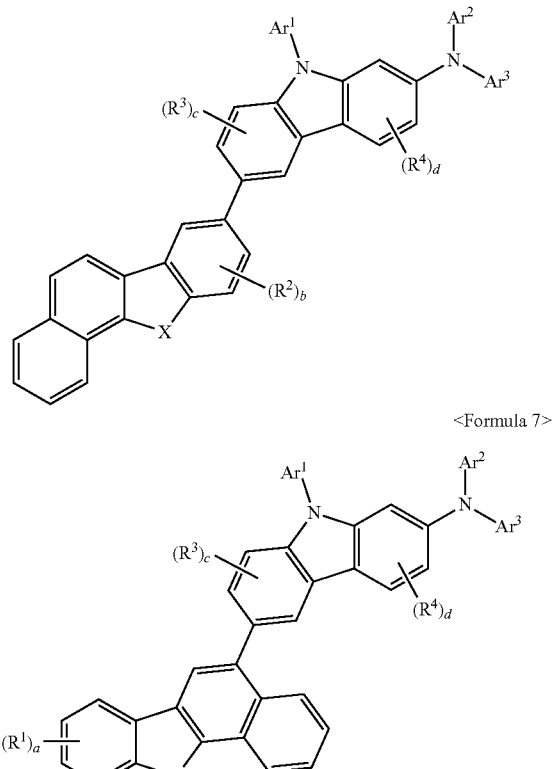
wherein a, b, c, d, $R^1$ to $R^4$, $Ar^1$ to $Ar^3$ are the same as defined in claim 1.
3. The compound of claim 1, wherein Formula 1 is represented by one of the following Formulas 4 to 9:
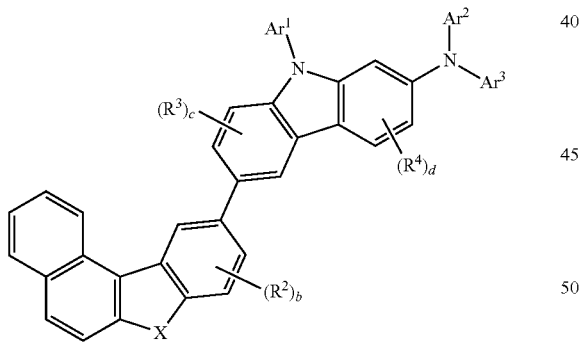
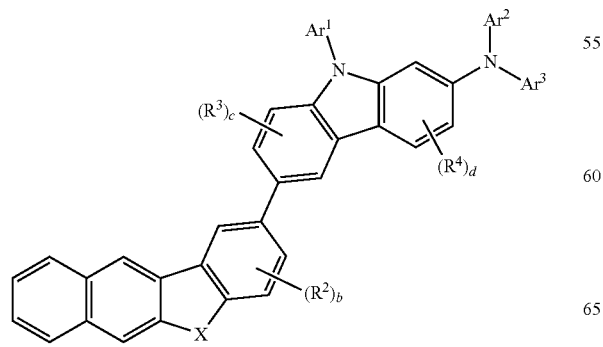
wherein X, a, b, c, d, $R^1$ to $R^4$, $Ar^1$ to $Ar^3$ are the same as defined in claim 1.
4. The compound of claim 1, wherein Formula 1 is one of the following compounds:

1-1
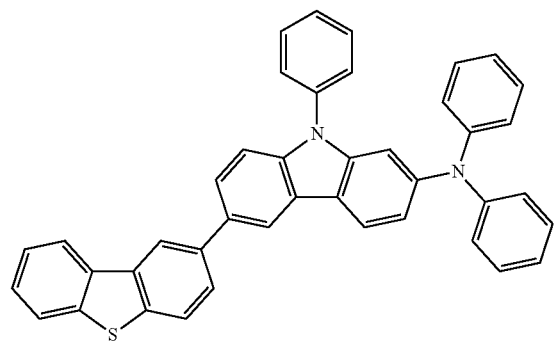
1-2
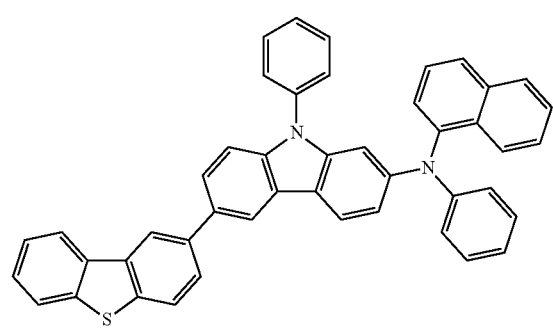
1-3
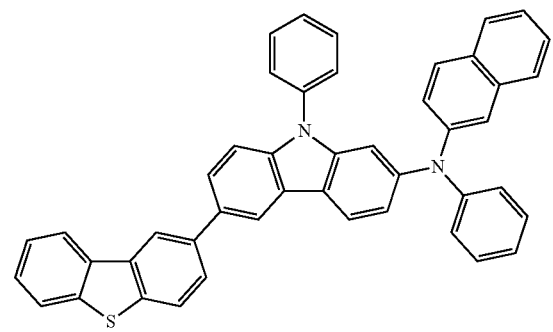
1-4
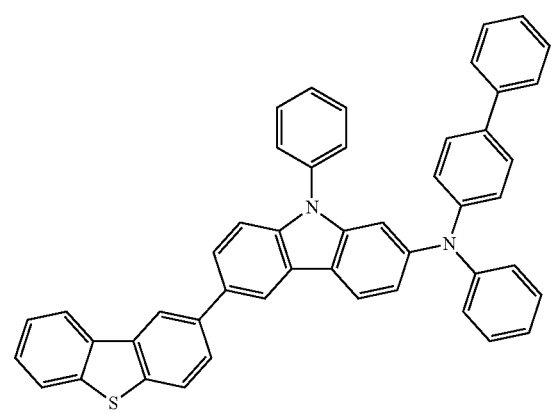
1-5
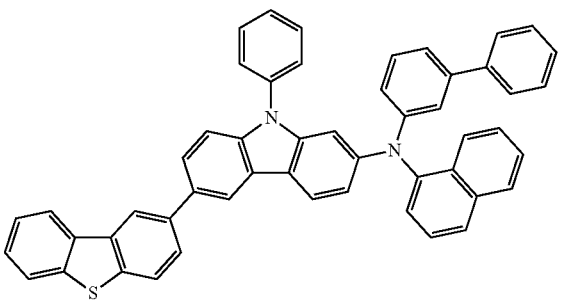
1-6
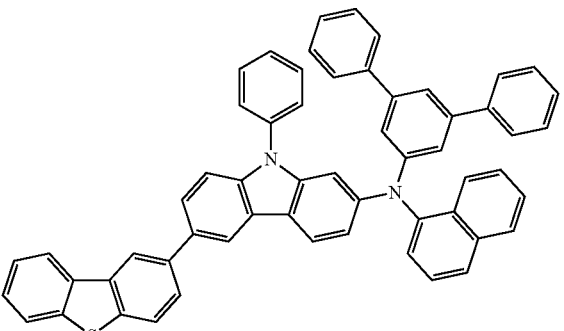
1-7
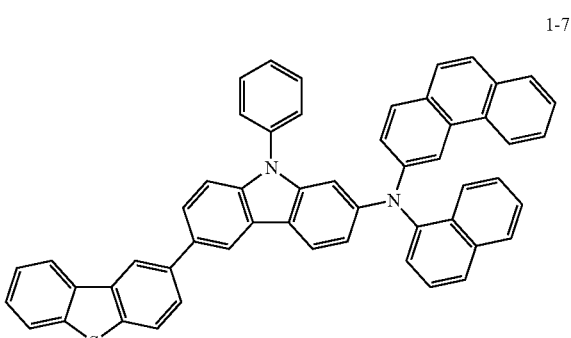
1-8
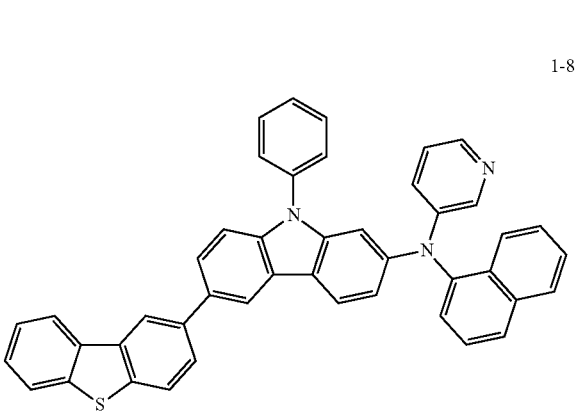

-continued
1-9
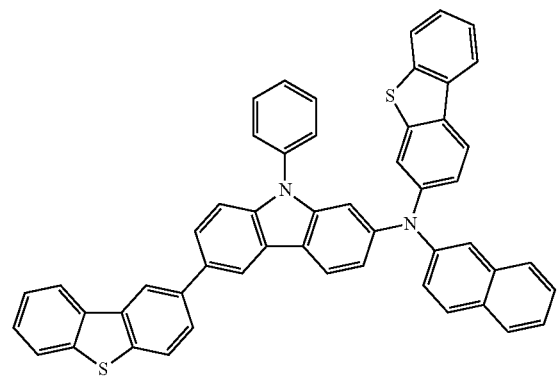
1-10
1-11
1-12
-continued
1-13
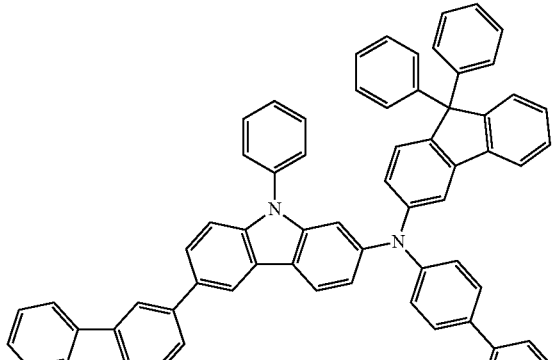
1-14
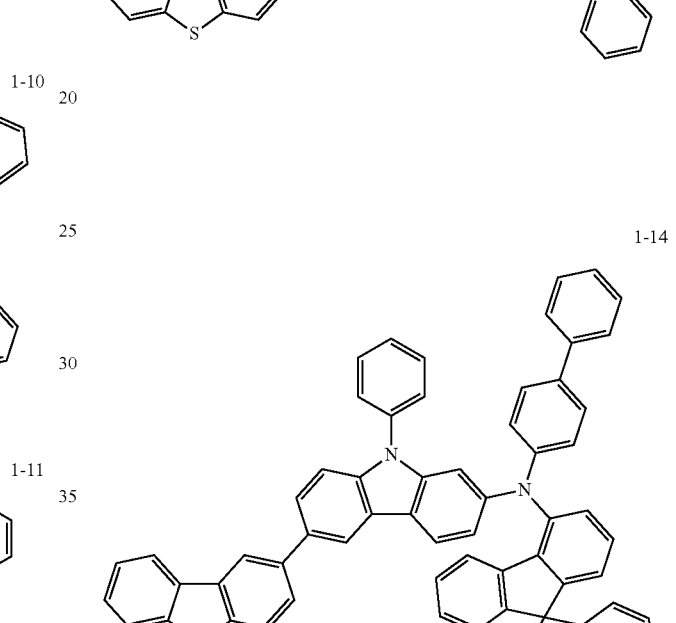
1-15
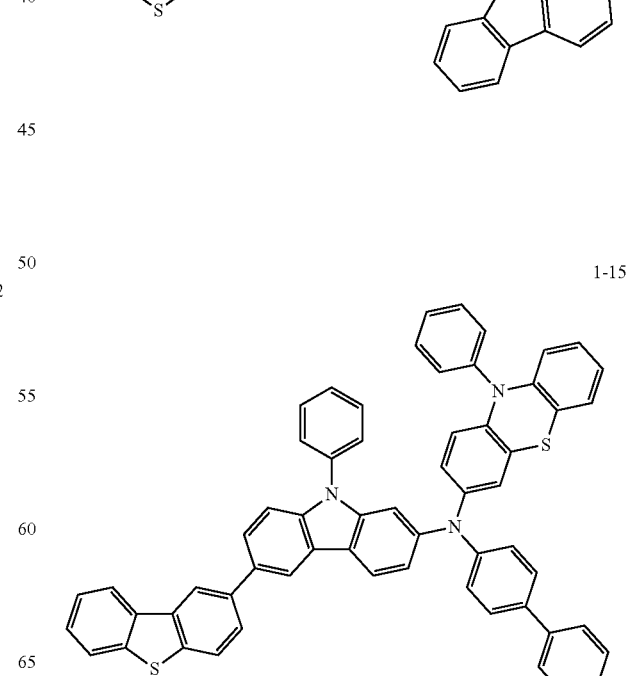

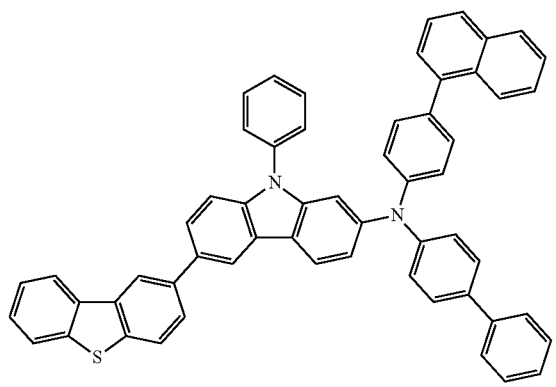
1-16
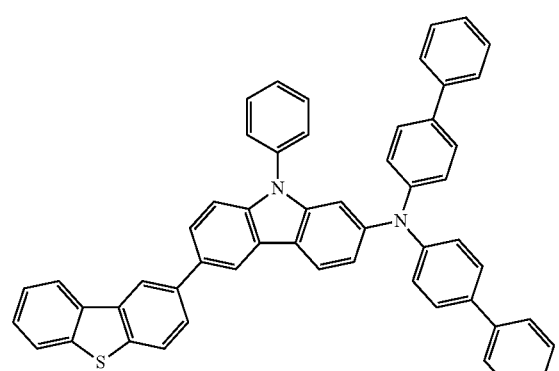
1-20
1-17
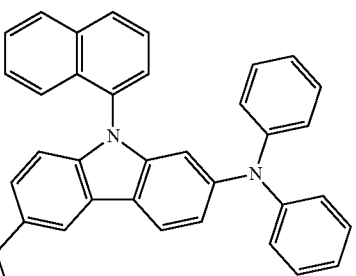
1-21
1-18
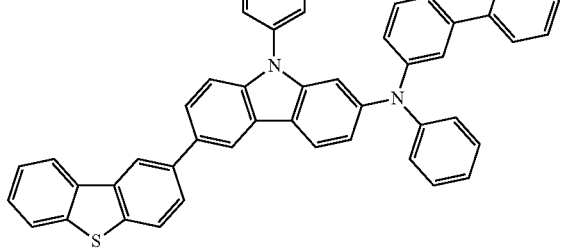
1-22
1-19
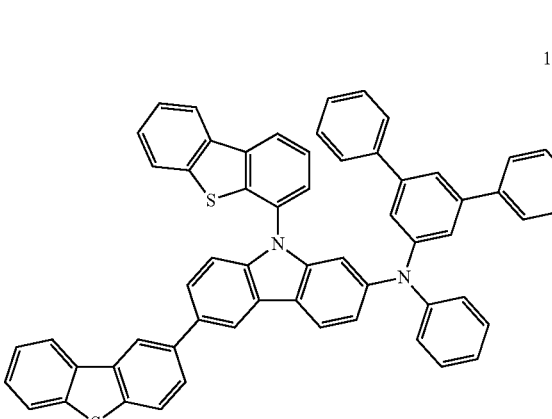
1-23
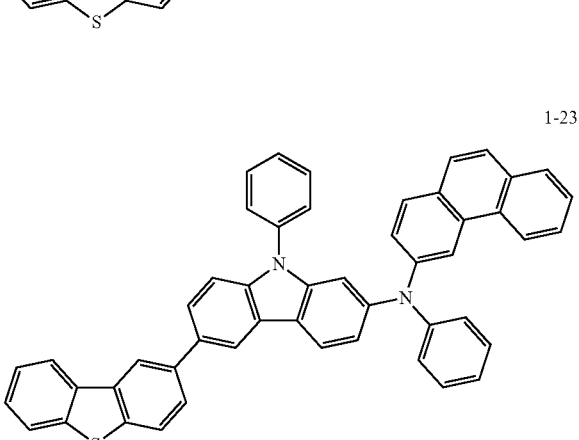

-continued
1-24
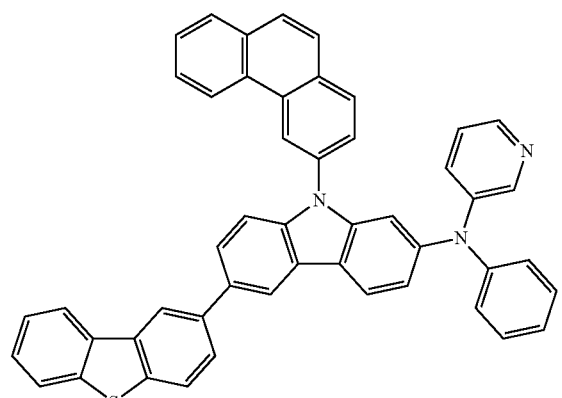
1-25
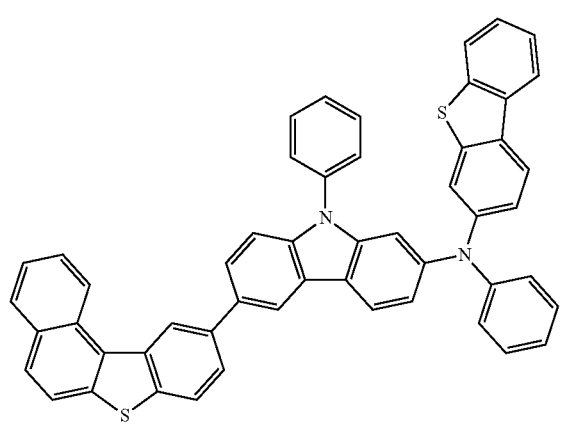
1-26
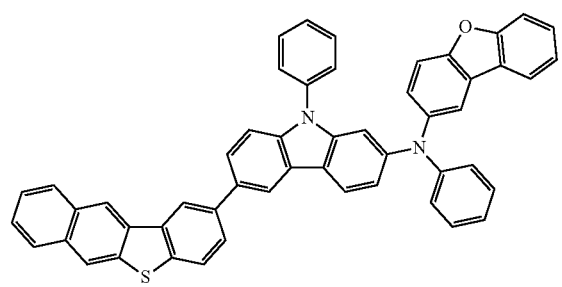
1-27
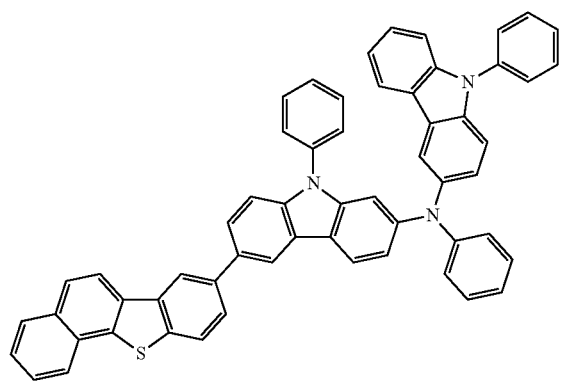
-continued
1-28
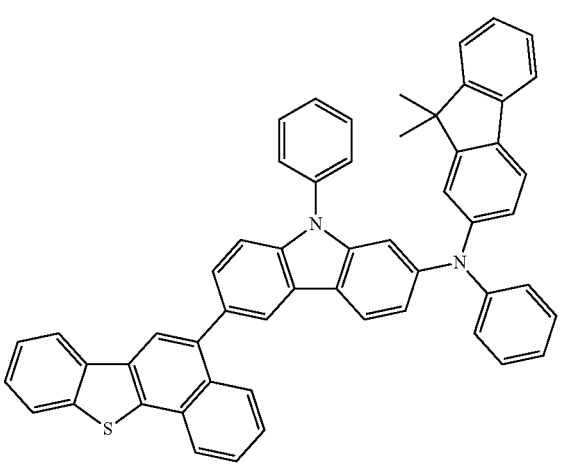
1-29
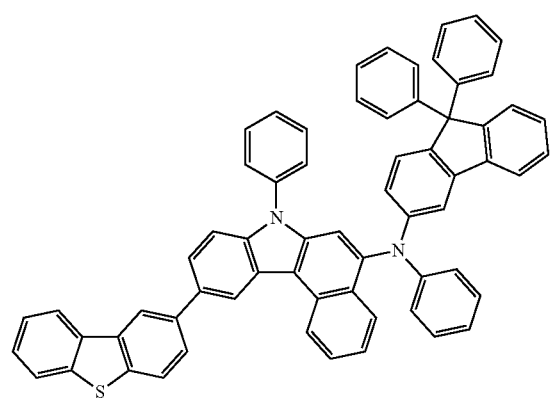
1-30
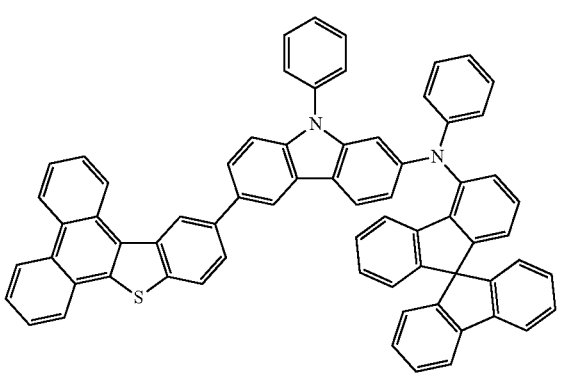

75
-continued
1-31
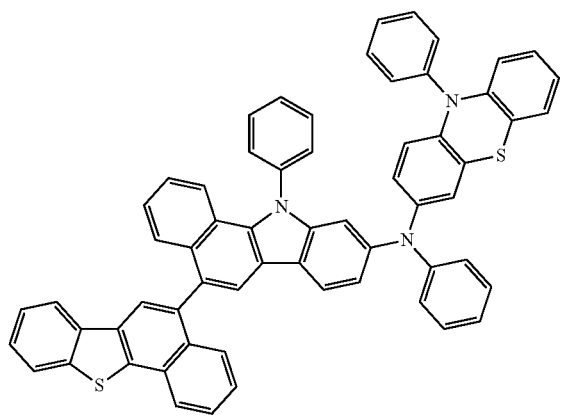
1-32
2-1
2-2
76
-continued
2-3
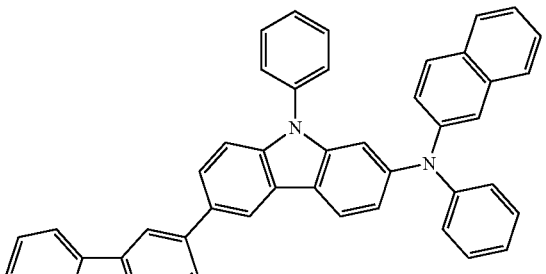
2-4
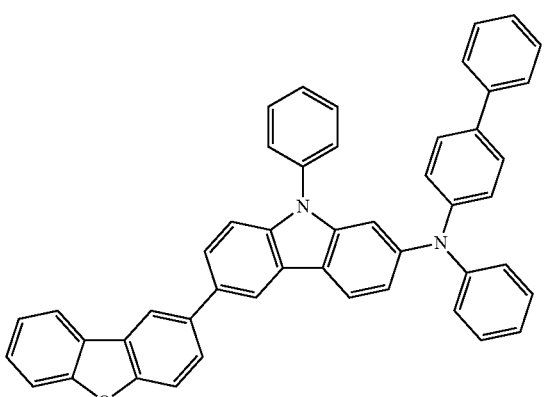
2-5
2-6
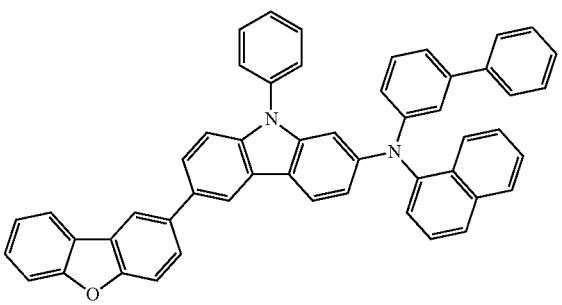
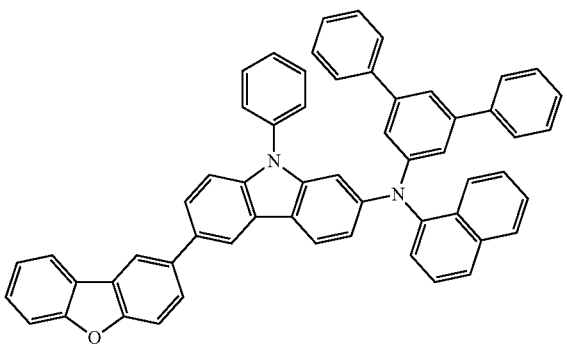

-continued
2-7
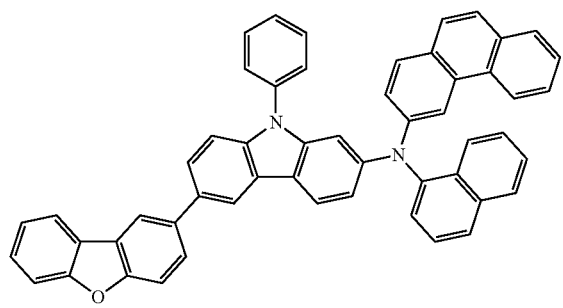
2-8
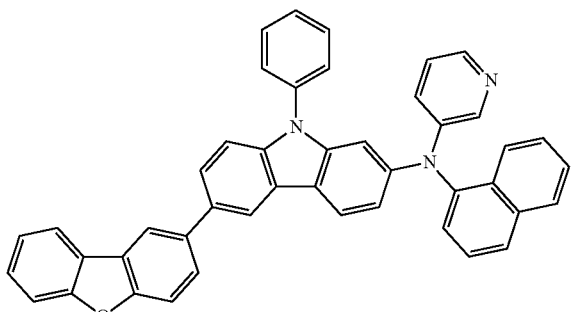
2-9
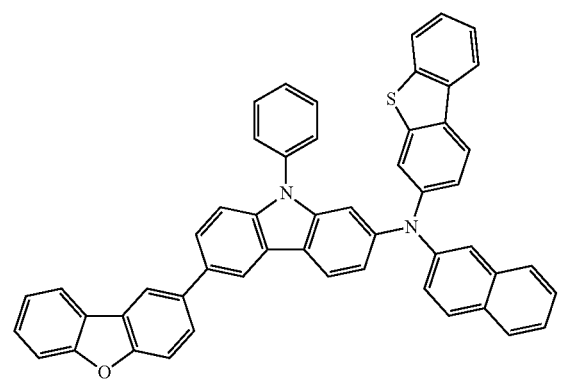
2-10
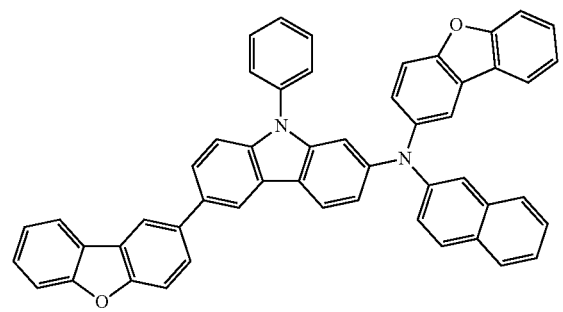
-continued
2-11
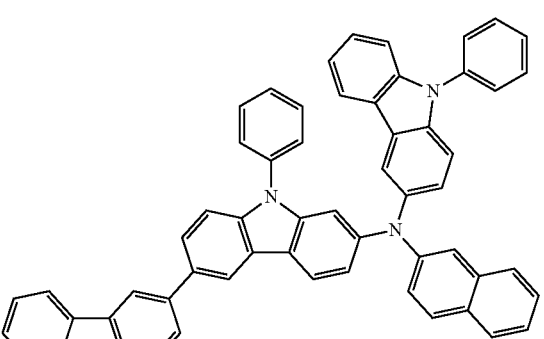
2-12
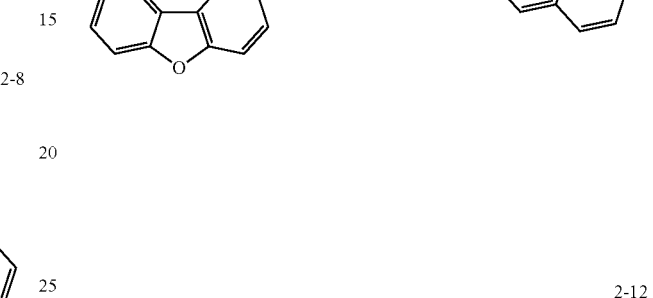
2-13
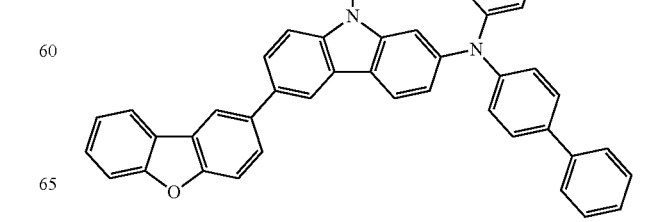

-continued
2-14
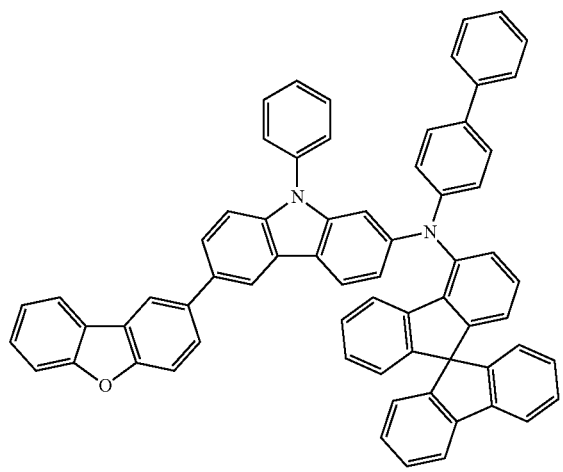
2-15
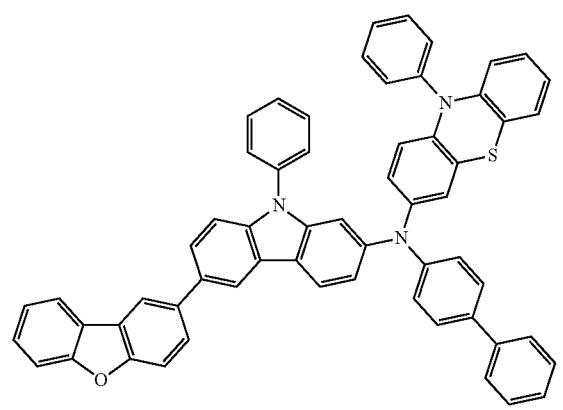
2-16
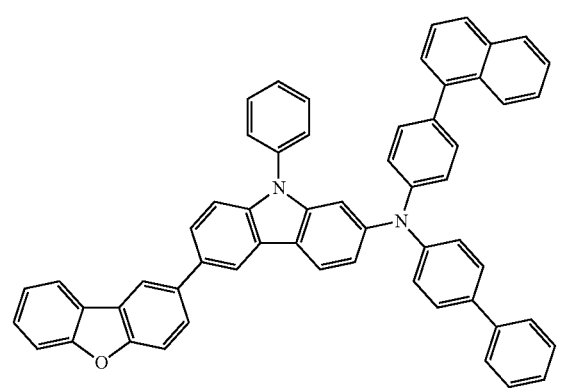
-continued
2-17
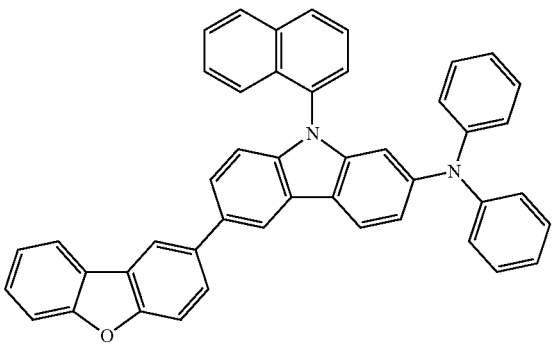
2-18
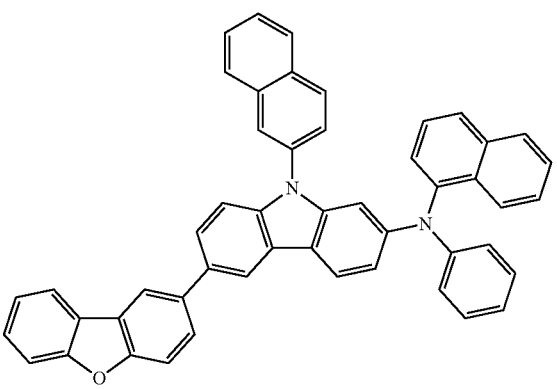
2-19
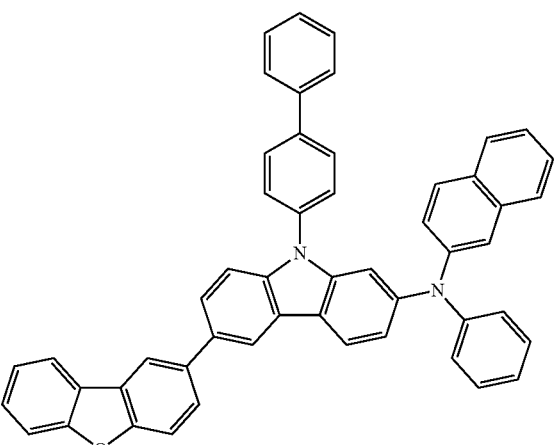
2-20
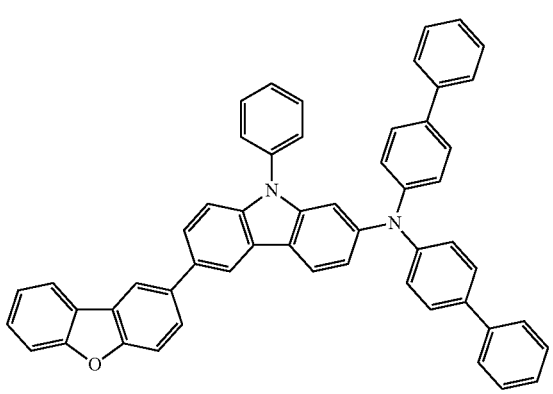

2-21
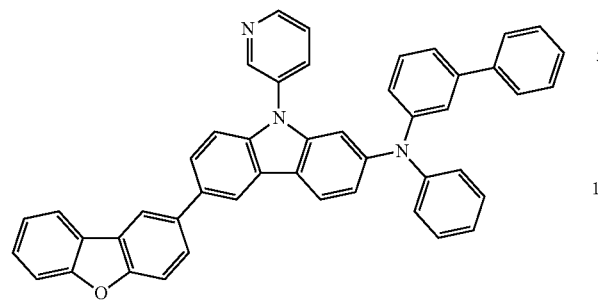
2-22
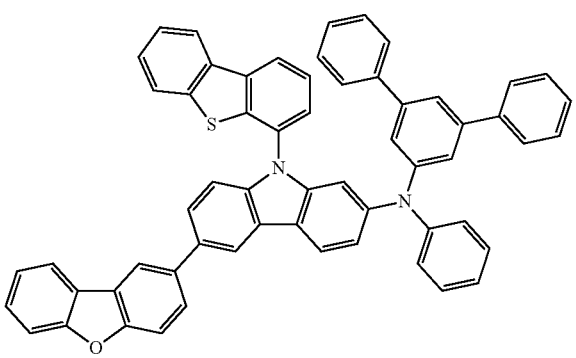
2-23
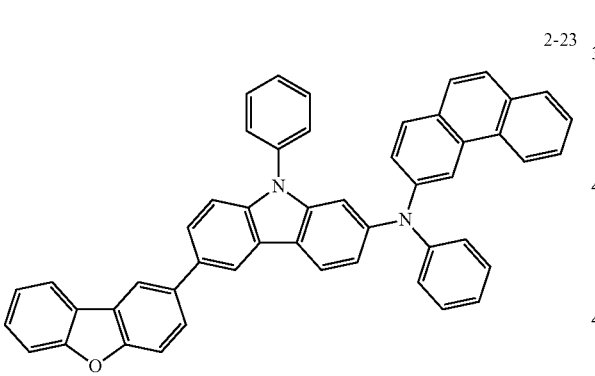
2-24
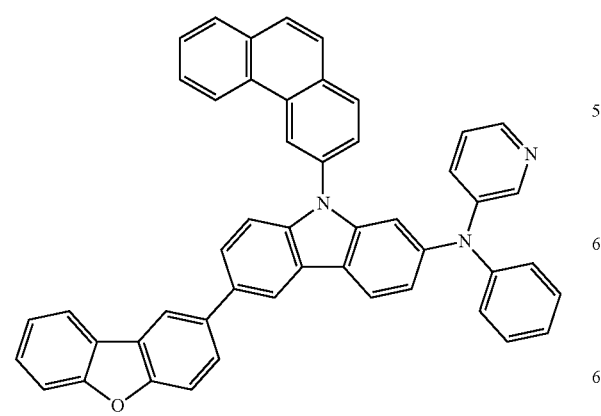
2-25
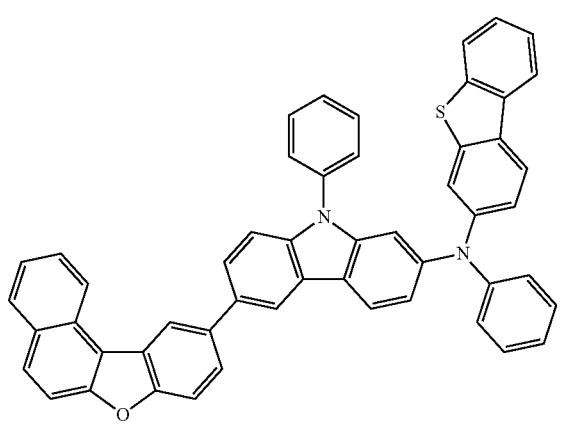
2-26
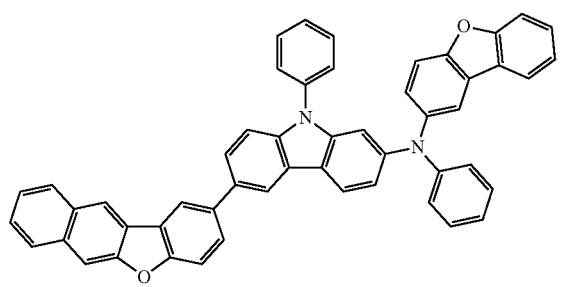
2-27
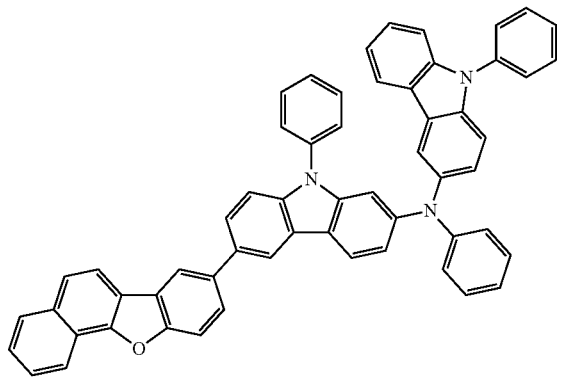
2-28
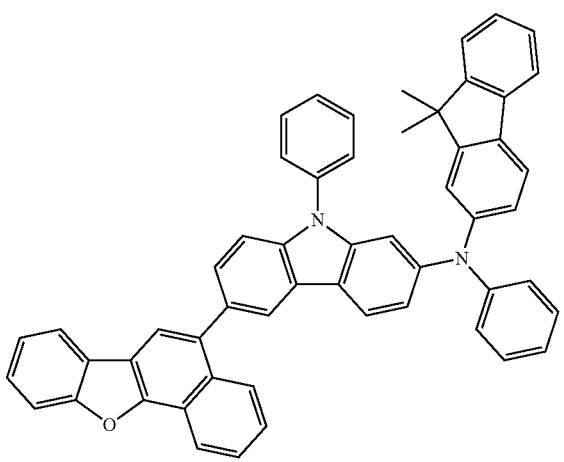

2-29

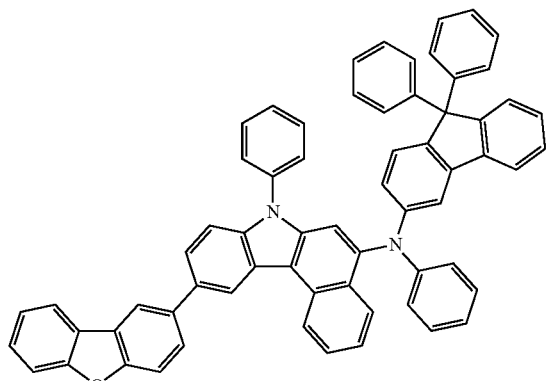

2-30

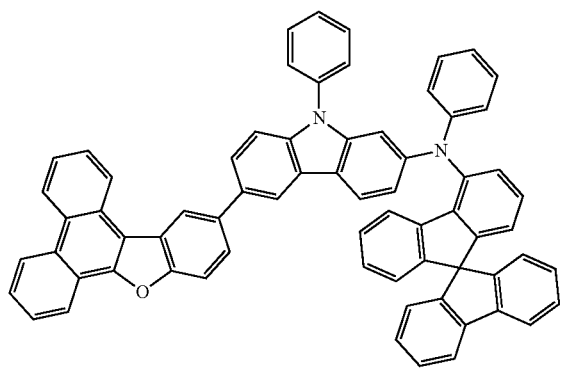

2-31

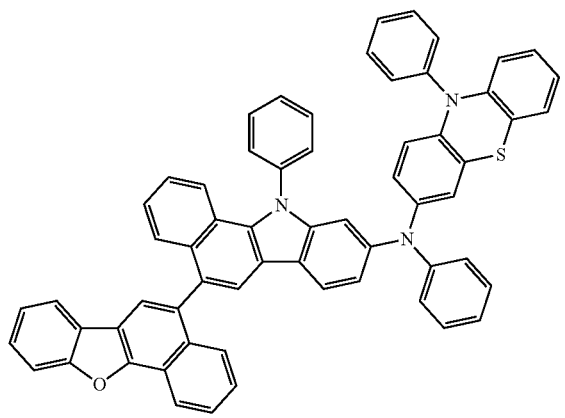

2-32

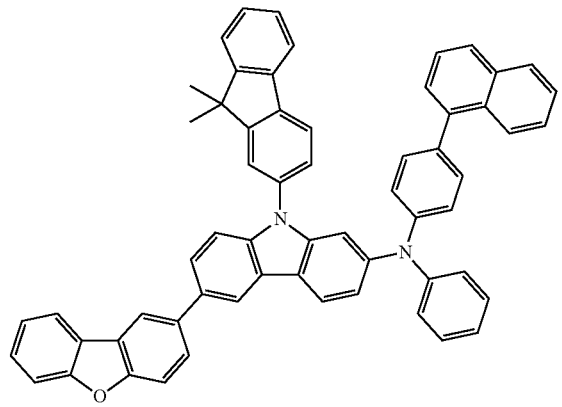

5. An organic electric element comprising a first electrode, a second electrode, and an organic material layer formed between the first electrode and the second electrode, wherein the organic material layer comprises the compound of claim 1.

6. The organic electric element of claim 5, wherein the compound is comprised as a single compound or a mixture of two or more kinds in at least one layer of a hole injection layer, a hole transport layer, an emission-auxiliary layer, a light emitting layer, an electron transport layer, an electron transport auxiliary layer and an electron injection layer of the organic material layer.

7. The organic electric element of claim 5 further comprising a layer for improving luminous efficiency formed on at least one side of sides of the first electrode and the second electrode, wherein at least one side is not facing the organic material layer.

8. The organic electric element of claim 5, wherein the organic material layer is formed by a process of spin coating, nozzle printing, inkjet printing, slot coating, dip coating or roll-to-roll.

9. An electronic device comprising a display device and a control unit for driving the display device, wherein the display device comprises the organic electric element of claim 5.

10. The electronic device of claim 9, wherein the organic electric element is an organic light emitting diode, an organic solar cell, an organic photo conductor, an organic transistor, or an element for monochromatic or white illumination.

* * * * *

UNITED STATES PATENT AND TRADEMARK OFFICE
CERTIFICATE OF CORRECTION

PATENT NO. : 11,081,649 B2
APPLICATION NO. : 16/078733
DATED : August 3, 2021
INVENTOR(S) : Lee et al.

It is certified that error appears in the above-identified patent and that said Letters Patent is hereby corrected as shown below:

In the Claims

Column 63, Claim 1, Formula 1:

Please delete " 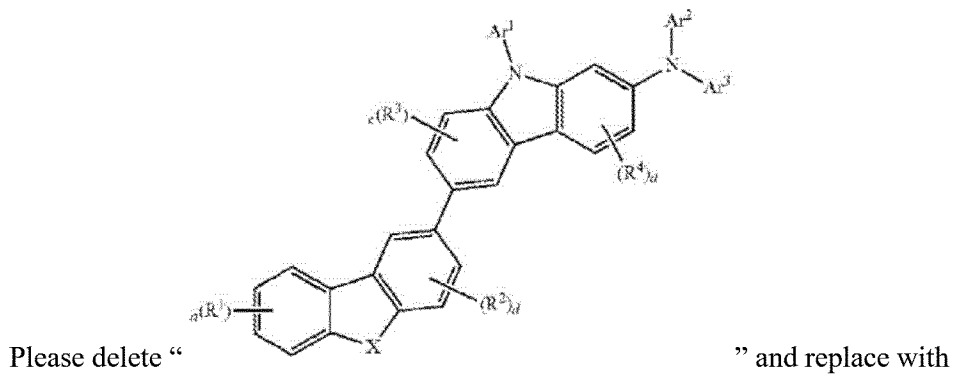 " and replace with

-- 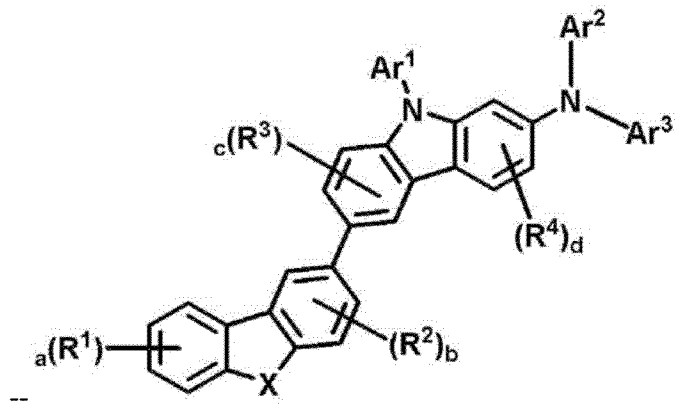 --

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*